(12) United States Patent
Wald et al.

(10) Patent No.: US 9,480,415 B2
(45) Date of Patent: Nov. 1, 2016

(54) ELECTROMAGNETIC COIL APPARATUSES FOR SURGICAL NAVIGATION AND CORRESPONDING METHODS

(71) Applicant: Medtronic Navigation, Inc., Louisville, CO (US)

(72) Inventors: Andrew Wald, Denver, CO (US); Bruce M. Burg, Louisville, CO (US); Steven L. Hartmann, Superior, CO (US); Brad Jacobsen, Erie, CO (US); Jeffrey Swetnam, Superior, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 406 days.

(21) Appl. No.: 13/871,625

(22) Filed: Apr. 26, 2013

(65) Prior Publication Data

US 2014/0323852 A1    Oct. 30, 2014

(51) Int. Cl.
    *A61B 5/06* (2006.01)
    *H01F 5/02* (2006.01)
    *A61B 17/00* (2006.01)

(52) U.S. Cl.
    CPC .............. *A61B 5/062* (2013.01); *A61B 34/20* (2016.02); *H01F 5/02* (2013.01); *A61B 2017/00725* (2013.01); *A61B 2034/2051* (2016.02); *A61B 2034/2068* (2016.02); *A61B 2034/2072* (2016.02); *A61B 2090/3958* (2016.02); *H01F 2005/027* (2013.01); *Y10T 29/49071* (2015.01)

(58) Field of Classification Search
    CPC .............. A61B 5/062; A61B 19/5244; A61B 2019/5251; A61B 34/20; A61B 2090/3958; A61B 2017/00725; A61B 2034/2051; A61B 2034/2072; A61B 2034/2068; H01F 5/02; H01F 2005/027; H01F 2005/022; Y01T 29/49071

See application file for complete search history.

(56) References Cited

U.S. PATENT DOCUMENTS

| 5,281,941 | A |   | 1/1994  | Bernstein       |         |
|-----------|---|---|---------|-----------------|---------|
| 5,425,367 | A | * | 6/1995  | Shapiro et al.  | 600/424 |
| 5,645,065 | A | * | 7/1997  | Shapiro et al.  | 600/424 |
| 5,913,820 | A | * | 6/1999  | Bladen et al.   | 600/407 |
| 5,963,120 | A | * | 10/1999 | Zaviska         | 336/208 |

(Continued)

FOREIGN PATENT DOCUMENTS

| DE | 3433003  A1 | 3/1986 |
|----|-------------|--------|
| DE | 10162693 C1 | 3/2003 |

(Continued)

OTHER PUBLICATIONS

International Search Report and Written Opinion mailed on Aug. 18, 2014 for PCT/US2014/034120 claiming benefit of U.S. Appl. No. 13/871,625, filed Apr. 26, 2013.

(Continued)

*Primary Examiner* — Long V Le
*Assistant Examiner* — Angela M Hoffa
(74) *Attorney, Agent, or Firm* — Harness, Dickey

(57) ABSTRACT

An electromagnetic device includes a jig and multiple wires. The jig includes a center member and coil-separating blocks. The coil-separating blocks protrude from the center member and are separated from each other to provide a coil channels. Each of the wires is wrapped on the jig, around the center member, and in one of the coil channels to form one of a multiple coils. Each of the coils is configured to connect to an electromagnetic navigation system and generate respective electromagnetic fields to be emitted relative to a subject.

20 Claims, 15 Drawing Sheets

(56) References Cited

U.S. PATENT DOCUMENTS

| | | | |
|---|---|---|---|
| 6,061,644 A * | 5/2000 | Leis | 702/153 |
| 6,380,732 B1 * | 4/2002 | Gilboa | 324/207.17 |
| 6,611,141 B1 * | 8/2003 | Schulz et al. | 324/226 |
| 6,822,570 B2 * | 11/2004 | Dimmer et al. | 340/572.1 |
| 6,977,504 B2 * | 12/2005 | Wright et al. | 324/326 |
| 7,026,927 B2 * | 4/2006 | Wright et al. | 340/539.12 |
| 7,573,258 B2 * | 8/2009 | Anderson | 324/207.17 |
| 7,658,196 B2 * | 2/2010 | Ferreri et al. | 128/899 |
| 7,684,849 B2 * | 3/2010 | Wright et al. | 600/424 |
| 7,782,046 B2 * | 8/2010 | Anderson | 324/207.17 |
| 7,809,421 B1 * | 10/2010 | Govari | 600/407 |
| 7,816,915 B2 * | 10/2010 | Susel et al. | 324/258 |
| 7,911,202 B2 * | 3/2011 | Anderson | 324/207.15 |
| 7,924,000 B2 * | 4/2011 | Susel et al. | 324/261 |
| 8,301,226 B2 * | 10/2012 | Csavoy et al. | 600/424 |
| 8,452,375 B2 * | 5/2013 | Krag et al. | 600/424 |
| 8,467,852 B2 * | 6/2013 | Csavoy et al. | 600/424 |
| 8,644,907 B2 | 2/2014 | Hartmann et al. | |
| 2002/0193685 A1 * | 12/2002 | Mate et al. | 600/424 |
| 2003/0052785 A1 * | 3/2003 | Gisselberg et al. | 340/572.8 |
| 2003/0192557 A1 * | 10/2003 | Krag et al. | 128/898 |
| 2004/0125916 A1 * | 7/2004 | Herron et al. | 378/65 |
| 2004/0133101 A1 * | 7/2004 | Mate et al. | 600/426 |
| 2004/0138555 A1 * | 7/2004 | Krag et al. | 600/424 |
| 2004/0158146 A1 * | 8/2004 | Mate et al. | 600/427 |
| 2005/0261570 A1 * | 11/2005 | Mate et al. | 600/411 |
| 2007/0129629 A1 * | 6/2007 | Beauregard et al. | 600/424 |
| 2007/0157828 A1 * | 7/2007 | Susel et al. | 101/35 |
| 2007/0244388 A1 * | 10/2007 | Sato | A61B 1/00147 600/424 |
| 2009/0112128 A1 | 4/2009 | Schiff et al. | |
| 2009/0216113 A1 * | 8/2009 | Meier et al. | 600/424 |
| 2009/0299174 A1 * | 12/2009 | Wright et al. | 600/424 |
| 2010/0160771 A1 * | 6/2010 | Gielen et al. | 600/424 |
| 2010/0305427 A1 * | 12/2010 | Huber et al. | 600/424 |
| 2010/0321015 A1 * | 12/2010 | Susel et al. | 324/258 |
| 2012/0046542 A1 * | 2/2012 | Csavoy et al. | 600/424 |
| 2014/0051983 A1 * | 2/2014 | Schroeder et al. | 600/424 |
| 2014/0303489 A1 * | 10/2014 | Meier et al. | 600/424 |

FOREIGN PATENT DOCUMENTS

| | | |
|---|---|---|
| EP | 0122133 A1 | 10/1984 |
| EP | 1174082 A1 | 1/2002 |
| EP | 1481637 A1 | 12/2004 |
| EP | 1806756 A2 | 7/2007 |
| WO | WO-2004073283 A2 | 8/2004 |
| WO | WO-2011020389 A1 | 2/2011 |
| WO | WO-2011136998 A1 | 11/2011 |
| WO | WO-2012098851 A1 | 7/2012 |

OTHER PUBLICATIONS

International Preliminary Report on Patentability mailed on Nov. 5, 2015 for PCT/US2014/034120 claiming benefit of U.S. Appl. No. 13/871,625, filed Apr. 26, 2013.

International Search Report and Written Opinion mailed Jun. 16, 2016 for PCT/US2016/023872 which claims the benefit of U.S. Appl. No. 14/673,994, filed on Mar. 24, 2016.

* cited by examiner

ELECTROMAGNETIC COIL APPARATUSES FOR SURGICAL NAVIGATION AND CORRESPONDING METHODS

FIELD

The disclosure relates to electromagnetic navigation procedures, and more particularly to coil arrays for generating or receiving electromagnetic fields.

BACKGROUND

This section provides background information related to the present disclosure which is not necessarily prior art.

Electromagnetic-based navigation procedures include a surgeon using a navigation system to track a position of a surgical instrument in a three dimensional (3-D) space. In addition to the surgical instrument, the navigation system also includes a localizer and a processor. The localizer generates electromagnetic fields (or first signals), which are detected by the surgical instrument. The surgical instrument generates and/or outputs second signals in response to the first signals. The processor then determines a position of the surgical instrument based on the second signals.

The navigation system can assist in determining a location of a tracked device on a pointer probe and/or on a surgical instrument, such as a scalpel, a catheter, a suction device, or a deep brain stimulation probe. A pointer probe may be used to track a position of an instrument not having a tracking device. A tracked device may refer to the pointer probe, the surgical instrument or a device on the pointer probe or the surgical instrument. The position of the tracked device can be determined relative to a subject (e.g., a patient). The position of the tracked device can be illustrated on a display relative to the subject by superimposing an icon or image of the tracked device on an image of the subject.

Image data of the subject is often acquired for display prior to, during, and/or after a procedure on the subject. An image of the subject and the corresponding image data can be registered to the subject. The image data can define a first three-dimensional space (or image space). The subject can define a second three-dimensional space (or physical space) to which the image data is registered. Registration can be performed using multiple processes.

An electromagnetic (EM) navigation system can be used to acquire or determine navigation information, including tracked locations of various tracking devices and relative locations to registered image data. In an EM navigation system, EM fields are generated by a localizer and sensed by one or more tracking devices. The localizer can be positioned near or relative to the subject space. The tracking devices can be positioned on or in association with a surgical instrument. The EM fields can be affected by conductive or magnetic materials located in an area of the EM fields. Examples of conductive materials are metals, conductive polymers, and impregnated polymeric materials. An example of a magnetic material is soft ferromagnetic iron.

SUMMARY

This section provides a general summary of the disclosure, and is not a comprehensive disclosure of its full scope or all of its features.

An electromagnetic device is provided and includes a jig and multiple wires. The jig includes a center member and coil-separating blocks. The coil-separating blocks protrude from the center member and are separated from each other to provide a coil channels. Each of the wires is wrapped on the jig, around the center member, and in one of the coil channels to form one of a multiple coils. Each of the coils is configured to connect to an electromagnetic navigation system and generate respective electromagnetic fields to be emitted relative to a subject.

In other features, another electromagnetic field device is provided and includes a jig and a wire. The jig includes a pair of end members and a center member. The center member is disposed between the pair of end members. The pair of end members and the center member together provide a coil channel. The coil channel includes dividers. The center member, the dividers, and the end member together provide wire channels. The wire is wrapped on the center member and in the wire channels to provide a coil. The coil is configured to connect to an electromagnetic navigation system and generate an electromagnetic field to be emitted relative to a subject.

In other features, a method is provided and includes forming a first jig to include a center member and coil-separating blocks. The coil-separating members protrude from the center member and provide coil channels. The coil channels are segregated by each other and include a first channel and a second channel. A first wire is wrapped on the first jig, around the center member, and in the first channel to form a first coil. A second wire is wrapped on the first jig, around the center member and the first coil, and in the second channel to form a second coil. The first wire and the second wire are configured to connect to an electromagnetic navigation system and generate respective electromagnetic fields to be emitted relative to a subject.

In other features, another method is provided and includes determining a number of jigs, including a first jig, to be included in a transmit coil array. The jigs are formed. Each of the jigs is formed to include a center member and a pair of end members. The center member is disposed between the pair of end members. The pair of end members and the center member together provide a coil channel. Wires are wrapped on the jigs. Each of the wires is wrapped on one of the center members and in one of the coil channels of a respective one of the jigs to provide a coil. The jigs are mounted on a base plate to form the transmit coil array. Each of the jigs is mounted in a respective location on the base plate. The coils are configured to connect to an electromagnetic navigation system and generate electromagnetic fields to be emitted relative to a subject.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
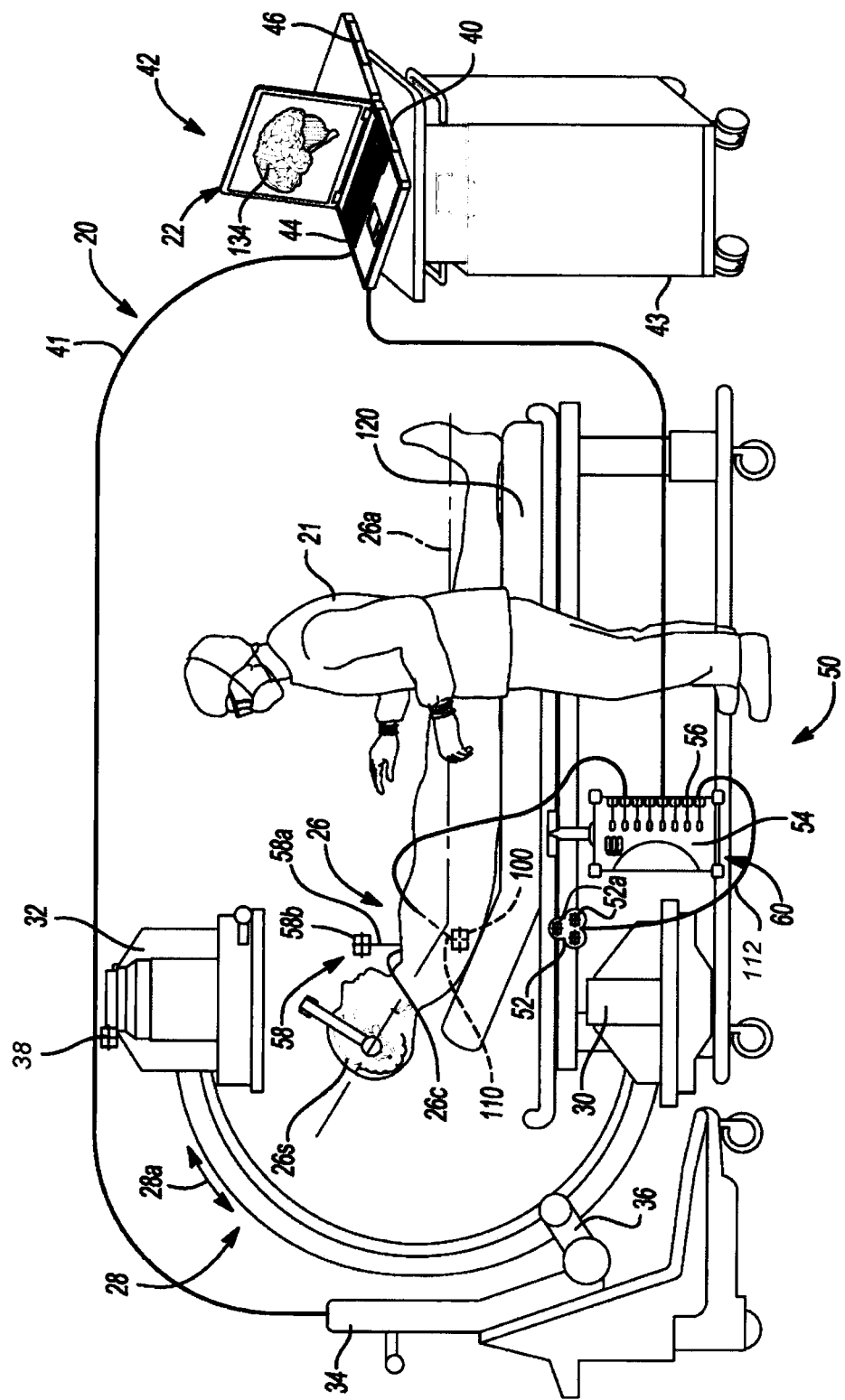
FIG. 1 is an environmental view of an operating room having an electromagnetic navigation system in accordance with the present disclosure.

Example embodiments will now be described more fully with reference to the accompanying drawings.

The following description is merely exemplary in nature and is not intended to limit the present disclosure, application, or uses. It should be understood that throughout the drawings, corresponding reference numerals indicate like or corresponding parts and features.

A localizer of an EM navigation system may include a transmit coil array (TCA). Although the localizers referred to and/or disclosed herein are primarily described as including TCAs (or coil arrays) for transmitting signals, the TCAs may be used for receiving signals. The TCA can include multiple sets of EM coils. Each set of the EM coils may include three orthogonally positioned coils that are used to generate EM fields. Other arrangements are disclosed below. The coil arrangements include singular coil arrangements and coil arrangements with coils that are not orthogonal to each other. Orthogonally positioned coils have respective center axes that are at right angles relative to each other. EM navigation is dependent on a precise and lengthy calibration process for calibrating the TCA. The calibration process can also cause a "bottleneck" in a manufacturing process of a navigation system.

The calibration process is primarily performed due to inconsistencies, irregularities, and varying differences in TCAs. This includes differences in coil placements, number of windings of each coil, lengths of coil wires, sizes of coils, spacing between coils, etc. The following disclosed implementations provide TCAs that can minimize calibration processes of TCAs and/or eliminate the need for calibrating TCAs. Examples of TCAs and corresponding manufacturing methods are shown in FIGS. 2-12 and 14-15. An example EM navigation system 20 is shown in FIG. 1. The EM navigation system 20 may include any of the TCAs shown and/or described with respect to FIGS. 2-12 and 14-15.

Although the EM navigation system 20 is primarily described with respect to performing a procedure on a human patient, the EM navigation system 20 may be used to perform a procedure on other animate and/or inanimate subjects. Also, the implementations disclosed herein may be applied to other EM systems and for purposes other than for position tracking of devices. For example, the implementations may be used to generate EM fields in a transcranial magnetic stimulation system. Also, procedures disclosed herein can be performed relative to a volume, a mechanical device, and/or an enclosed structure. The volume may be of an animate or inanimate object. The subject can be an object that includes an enclosed mechanical device.

The EM navigation system 20 performs a guided procedure. The guided procedure can be, for example, a surgical procedure, a neural procedure, a spinal procedure, and an orthopedic procedure. The EM navigation system 20 allows a user, such as a surgeon 21, to view on a display 22 a position of an instrument 110 in a coordinate system. The coordinate system can be related to an image, such as in an image guided procedure, or can be related to an imageless procedure.

The EM navigation system 20 can operate as an image-based system or as an imageless system. While operating as an imageless system, the EM navigation system 20 can register the subject space to a graphical display representing an area of the subject 26, rather than to both the subject space and an image space. Image data of the subject 26 need not be acquired at any time, although image data can be acquired to confirm various locations of instruments or anatomical portions of the subject 26. Positions of the subject 26 can be tracked and positions of the instrument 110 relative to the subject 26 can be tracked.

While operating as an imageless system, a position of an anatomical structure can be determined relative to the instrument and the positions of the anatomical structure and the instrument can be tracked. For example, a plane of an acetabulum can be determined by touching several points with the instrument 110. As another example, a position of a femur can be determined in a similar manner. The position of the instrument 110 and the anatomical structure can be shown on a display with icons or graphics. The display, however, may not show actual image data captured of the subject 26. Other data can be provided, such as atlas data or morphed atlas data. The atlas data can be image data that is generated or generalized from the subject 26. For example, a brain atlas can be generated based on detail analysis of image data of a brain of a patient. Operation of the EM navigation system 20 as an image based system is further described below.

The EM navigation system 20 can be used to navigate or track rigid and flexible instruments. Examples of rigid instruments include drill motors, probes, awls, drill bits, large outer diameter (OD) needles, large or inflexible implants, etc. Examples of flexible instruments include catheters, probes, guide wires, small OD needles, small or flexible implants, deep brain stimulators, electrical leads, etc. The instrument 110 can be used in any region of a body of the subject 26. The EM navigation system 20 and instrument 110 can be used in various minimally invasive procedures, such as arthroscopic, percutaneous, stereotactic, or in an open procedure.

Although the EM navigation system 20 is described as acquiring image data using an imaging device 28, other data may be acquired and/or used, such as patient and non-patient specific data. The imaging device 28 acquires pre-, intra-, or post-operative image data and/or real-time image data of a subject 26. The imaging device 28 can be, for example, a fluoroscopic x-ray imaging device that may be configured as a C-arm having an x-ray source 30 and an x-ray receiving device 32. Other imaging devices may be included and mounted on the imaging device 28. Calibration and tracking targets and radiation sensors may be included. The imaging device 28 may be part of a fluoroscopic system, such as a bi-plane fluoroscopic system, a ceiling fluoroscopic system, a cath-lab fluoroscopic system, a fixed C-arm fluoroscopic system, an isocentric C-arm fluoroscopic system, a three dimensional fluoroscopic system, etc.

The EM navigation system 20 further includes an imaging device controller 34. The imaging device controller 34 controls the imaging device 28 to (i) capture x-ray images received at the x-ray receiving section 32, and (ii) store the x-ray images. The imaging device controller 34 may be separate from the imaging device 28 and/or control the rotation of the imaging device 28. For example, the imaging device 28 can move in the direction of arrow 28a or rotate about a longitudinal axis 26a of the subject 26. This allows anterior or lateral views of the subject 26 to be imaged. Each of these movements involves rotation about a mechanical axis of the imaging device 28 via a member 36.

X-rays can be emitted from the x-ray source 30 and received at the x-ray receiving section 32. The x-ray receiving section 32 can include a camera that can create the image data from the received x-rays. Other suitable imaging devices and/or systems may be used to create or capture image data. For example, a magnetic resonance imaging system or a positron emission tomography system may be used. Further, an imager tracking device 38 may be included to track a position of the x-ray receiving section 32 of the imaging device 28 at selected times by, for example, the C-arm controller 34. The image data can then be forwarded from the C-arm controller 34 to a processing module of a navigation computer 40 wirelessly or via a link 41. The navigation computer 40 can include a processing module that is configured to execute instructions to perform a procedure.

A work station 42 can include the navigation computer 40, the display 22, a user interface 44, and an accessible memory system 46. The image data may be transmitted from the C-arm controller 34 to the work station 42 or to a tracking system 50. The navigation computer 40 may be a portable computer, such as a laptop computer or a tablet computer.

The work station 42 displays the image data as an image on the display 22. The user interface 44 may be a keyboard, a mouse, a touch pen, a touch screen, or other suitable interface. The user interface 44 allows the user 21 to provide inputs to control the imaging device 28, via the C-arm controller 34, or adjust display settings of the display 22. The work station 42 can also be used to control and receive data from a coil array controller (CAC) 54 having a navigation device interface (NDI) 56.

While the imaging device 28 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative, computed tomography (CT), single photo emission computed tomography (SPECT), and/or planar gamma scintigraphy (PGS) imaging devices may be used. Any of these imaging devices may be used to acquire 2D, 3D or 4D pre- or post-operative and/or real-time images or image data of the subject 26. The images may also be obtained and displayed, generally, in two or three dimensions. In more advanced forms, 3D surface rendering regions are achieved of the subject, which may be rendered or changed in time (fourth dimension). The 3D surface rendering regions may be achieved by incorporating subject data or other data from an atlas or anatomical model map or from pre-operative image data captured by MRI, CT, or echocardiography modalities.

Image data sets from hybrid modalities, such as positron emission tomography (PET) combined with CT, or single photon emission computer tomography (SPECT) combined with CT, can also provide functional image data superimposed onto anatomical data to be used to reach target sites within the subject 26. The imaging device 28, as shown in FIG. 1, can provide a virtual bi-plane image using a single-head C-arm fluoroscope by rotating the imaging device 28 about at least two planes. The two planes could be orthogonal planes and used to generate two-dimensional images. The two-dimensional images can be converted to three-dimensional volumetric images. By acquiring images in more than one plane, an icon representing the location of the instrument, introduced and advanced in the subject 26, may be superimposed in more than one view on the display 22. This allows simulated bi-plane or multi-plane views, including two and three-dimensional views. The instrument 110 may include, for example, an impacter, a stylet, a reamer driver, taps, a drill, deep brain stimulators, electrical leads, needles, implants, probes, or other instrument.

The EM navigation system 20 further includes a tracking system 50. The tracking system 50 includes a localizer 52, which may also be referred to as a transmit coil array (TCA), a tracking array, or a transmit coil assembly. Examples of localizers and corresponding components are shown in FIGS. 2-12. The TCA 52 includes coil arrays 52a that can transmit or receive. The tracking system 50 includes the CAC 54. The localizer 52, an instrument tracking device 100 of an instrument 110, and a dynamic reference frame (DRF) 58 are connected to the CAC 54 via the NDI 56. The CAC 54 and the NDI 56 can be provided in a CAC/NDI container 60. The NDI 56 may have communication ports that communicate with the localizer 52, the instrument tracking device 100 and/or the DRF 58 wirelessly or via wires.

The DRF 58 can include a DRF member 58a and a removable tracking device 58b. Alternatively, the DRF 58 can include the tracking device 58b that is formed integrally with the DRF member 58a. For example, the tracking device 58b can be connected directly to the subject 26. The tracking device 58b is a coil sensor that performs as an emitter or a receiver to sense one or more EM fields, or other appropriate device that can be tracked by the tracking system 50. Also, the tracking device 58b can be wired to other controllers, processors, modules, etc. of the EM navigation system 20.

The localizer 52 may be or include any of the TCAs shown and/or described with respect to FIGS. 2-14. Although a single localizer is shown in FIG. 1, additional localizers may be included to supplement EM fields generated by the localizer 52 and/or to provide additional EM fields. Supplementing EM fields generated by the localizer 52 and/or adding additional EM fields can increase a navigation area in which to perform a procedure and/or to accurately conduct navigation. The coil arrays 52a can transmit signals that are received by the DRF 58 and at least one tracking device (e.g., the instrument tracking device 100).

The tracking device 100 can be associated with the instrument 110 at a location that is generally positioned within the subject 26 during a procedure. The DRF 58 can then transmit and/or provide signals based upon the received/sensed signals of the generated fields from the localizer 52 and/or other localizers.

The tracking system 50 or components of the tracking system 50 may be incorporated into other systems or devices in the operating theatre. For example, one of the localizers can be incorporated into the imaging device 28. The transmitter coil arrays 52*a* can be attached to the x-ray receiving section 32 of the imaging device 28. The localizer 52 may be positioned at any location within the operating theatre. For example, the localizer 52 may be positioned at the x-ray source 30. Also, the localizer 52 can be positioned: within or on top of an operating room table 120; below the subject 26; on side rails associated with the table 120; or on the subject 26 and in proximity to a region being navigated within.

Also, the coil arrays 52*a* can include multiple coils (e.g., induction coils) that are each operable to generate distinct EM fields into the region being navigated, such as a region within the subject 26 (sometimes referred to as patient space). The coil arrays 52*a* are controlled or driven by the CAC 54. The CAC 54 can transmit a signal via a transmission line 112 to the localizer 52. The coil arrays 52*a* can have more than one coil that is driven by the CAC 54. The signal may be time division multiplexed or frequency division multiplexed. In one implementation, each of the coil arrays 52*a* includes at least three orthogonal coils that generate three orthogonal EM fields. The coil arrays 52*a* can include any number of coils. The localizer 52 can include any number of coil arrays. The coils can be oriented in various different positions and may not be in a position orthogonal to other coils. In this regard, each coil of the coil arrays 52*a* may be driven separately, at distinct times, simultaneously, and/or with respective current signals having predetermined frequencies.

Upon driving the coils in the coil arrays 52*a* with the coil array controller (or control module) 54, EM fields are generated within the subject 26 in the area where the medical procedure is being performed. The EM fields can induce currents in the tracking devices 58*b*, 100. In response to the induced currents, the tracking devices 58*b*, 100 generate signals, which are provided to the NDI 56 and can be forwarded to the CAC 54 and/or the navigation computer 40. The NDI 56 may provide electrical isolation for the EM navigation system 20. The NDI 56 can include amplifiers, filters and buffers to directly interface with the tracking devices 58*b*, 100. Alternatively, the tracking devices 58*b*, 100 may communicate wirelessly or via wires with the NDI 56.

The tracking device 100 can be in a handle or inserter that interconnects with an attachment and may assist in placing an implant. The instrument 110 can include a graspable or manipulable element at a proximal end and a sensor that can be fixed near the manipulable element or at a distal working end. The tracking device 100 can include an EM sensor to sense the EM fields generated by the localizer 52 and induce a current in the tracking device 100. As illustrated in FIG. 1, and discussed further herein, the tracking device 100 associated with the instrument 110 can also be placed completely or partially within the subject 26.

The DRF 58 can be connected to the NDI 56 to forward the information to the CAC 54 and/or the navigation computer 40. The DRF 58 may include a magnetic and/or EM field detector (e.g., the tracking device 58*b*). The DRF 58 may be fixed to the subject 26 and adjacent to the region where navigation is occurring such that any movement of the subject 26 is detected as relative motion between the localizer 52 and the DRF 58. The DRF 58 can be interconnected with the subject 26. Any relative motion is indicated to the CAC 54, which updates registration correlation and maintains accurate navigation. The DRF 58 may include a selected number of coils. For example, the coils may be mutually orthogonal with each other and share a center axis around which the coils are wound. The coils may be configured in various non-coaxial or co-axial coil configurations.

The DRF 58 may be affixed externally to the subject 26 and/or adjacent to a region of navigation (e.g., affixed on a skull of the subject 26, to a bone of the subject 26, or to skin of the subject 26). The DRF 58 may be affixed using an adhesive patch and/or a tensioning system. The DRF 58 may also be removably attachable to a fiducial marker. Fiducial markers can be anatomical landmarks and/or artificial members attached or positioned on the subject 26.

In operation, the EM navigation system 20 creates a map between points in image data or an image space and corresponding points in a subject space (e.g., points in an anatomy of a patient or in a patient space). After the map is created, the image space and subject space are registered to each other. This includes correlating position (location and orientations) in an image space with corresponding positions in a subject space (or real space). Based on the registration, the EM navigation system 20 may illustrate a position of the instrument 110 relative to an image of the subject 26 in a super-imposed image. For example, the instrument 110 can be illustrated relative to a proposed trajectory and/or a determined anatomical target. The work station 42 alone and/or in combination with the CAC 54 and/or the C-arm controller (or control module) 34 can: identify the corresponding point on the pre-acquired image or atlas model relative to the tracked instrument 110; and display the position on display 22 and relative to an image 134. This identification is known as navigation or localization. An icon representing a localized point or an instrument is shown on the display 22 within two-dimensional image planes, as well as on three and four dimensional images and models. The work station 42, the CAC 54, and the C-arm controller 34 and/or selected portions thereof can be incorporated into a single system or implemented as a single processor or control module.

To register the subject 26 to the image 134, the user 21 may use point registration by selecting and storing particular points from the pre-acquired images and then touching the corresponding points on the subject 26 with a pointer probe or any appropriate tracked device. The EM navigation system 20 analyzes the relationship between the two sets of points that are selected and computes a match, which allows for a correlation of every point in the image data or image space with its corresponding point on the subject 26 or the subject space.

The points that are selected to perform registration or form a map are the fiducial markers, such as anatomical or artificial landmarks. Again, the fiducial markers are identifiable on the images and identifiable and accessible on the subject 26. The fiducial markers can be artificial landmarks that are positioned on the subject 26 or anatomical landmarks that can be easily identified in the image data. The artificial fiducial markers can also form part of the DRF 58.

Any appropriate number of the fiducial markers can be provided with and/or separate from the DRF 58.

The EM navigation system 20 may also perform registration using anatomic surface information or path information (referred to as auto-registration). The EM navigation system 20 may also perform 2D to 3D registration by utilizing the acquired 2D images to register 3D volume images by use of contour algorithms, point algorithms or density comparison algorithms.

In order to maintain registration accuracy, the EM navigation system 20 tracks the position of the subject 26 during registration and navigation with the DRF 58. This is because the subject 26, DRF 58, and localizer 52 may all move during the procedure. Alternatively the subject 26 may be held immobile once the registration has occurred, such as with a head holder. Therefore, if the EM navigation system 20 does not track the position of the subject 26 or an area of an anatomy of the subject 26, any subject movement after registration would result in inaccurate navigation within the corresponding image. The DRF 58 allows the tracking system 50 to track the anatomy and can be used during registration. Because the DRF 58 is rigidly fixed to the subject 26, any movement of the anatomy or the localizer 52 is detected as the relative motion between the localizer 52 and the DRF 58. This relative motion is communicated to the CAC 54 and/or the processor 48, via the NDI 56, which updates the registration correlation to thereby maintain accurate navigation.

The DRF 58 can be affixed to any portion of the subject 26, and can be used to register the subject 26 to the image data, as discussed above. For example, when a procedure is being performed relative to a skull or cranium 26s, the DRF 58 can be interconnected with the cranium 26s.

The tracking system 50 can position the localizer 52 adjacent to the patient space to generate an EM field (referred to as a navigation field). Because points in the navigation field or patient space is associated with a unique field strength and direction, the tracking system 50 can determine the position (which can include location and orientation) of the instrument 110 by measuring the field strength and direction or components of the EM field at the tracking device 100. The DRF 58 is fixed to the subject 26 to identify the location of the subject 26 in the navigation field. The tracking system 50 continuously determines the relative position of the DRF 58 and the instrument 110 during localization and relates this spatial information to subject registration data. This enables image guidance of the instrument 110 within and/or relative to the subject 26.

To obtain a maximum accuracy it can be selected to fix the DRF 58 in each of at least 6 degrees of freedom. Thus, the DRF 58 or any tracking device, such as the tracking device 100, can be fixed relative to axial motion X, translational motion Y, rotational motion Z, yaw, pitch, and roll relative to a portion of the subject 26 to which the tracking device 58b is attached. Any appropriate coordinate system can be used to describe the various degrees of freedom. Fixing the DRF 58 relative to the subject 26 in this manner can assist in maintaining maximum accuracy of the EM navigation system 20.

The instrument 110 can be any appropriate instrument (e.g., a catheter, a probe, a guide, etc.) and can be used for various mechanisms and methods, such as delivering a material to a selected portion of the subject 26, such as within the cranium 26s. The material can be any appropriate material such as a bioactive material, a pharmacological material, a contrast agent, or any appropriate material. As discussed further herein, the instrument 110 can be precisely positioned (including location and orientation) via the EM navigation system 20 and otherwise used to achieve a protocol for positioning the material relative to the subject 26 in any appropriate manner, such as within the cranium 26s. The instrument 110 may also include a brain probe to perform deep brain stimulation.

As discussed above, an EM field can be generated by the localizer 52. The EM field is generated to define a navigation field. The navigation field can, however, be distorted by various distorting objects including the operating table 120, the imaging device 28, various instruments, etc.

Figure 2:
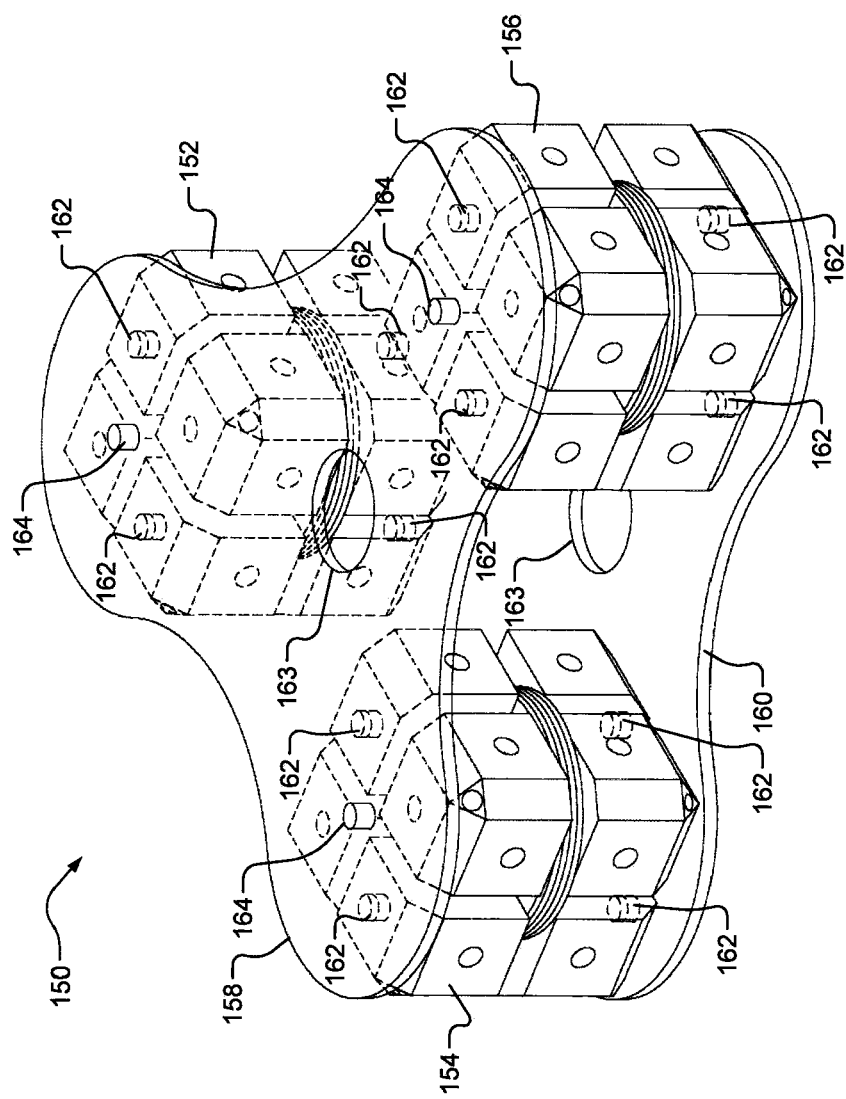
FIG. 2 is a perspective view of a transmit coil array including jigs each having a multiple coils in accordance with the present disclosure.

FIG. 2 shows a TCA 150 that includes jigs 152, 154, 156. Each of the jigs 152, 154, 156 has a coil array with respective coils. The jigs 152, 154, 156 are held in place relative to each other via end plates 158, 160. The jigs 152, 154, 156 are further described with respect to FIGS. 3-5. The end plates 158, 160 may include first tabs 162, which are inserted into respective holes in the jigs 152, 154, 156. An adhesive may be used to attach the first tabs 162 to the jigs 152, 154, 156. The end plates 158, 160 may also include mounting holes 163 and/or second tabs 164. The mounting holes 163 and/or second tabs 164 may be used to mount the TCA 150 onto an object in an EM navigation system and/or navigation theatre. For example, as shown in FIG. 1, the TCA 52 may be replaced with the TCA 150 and be attached to the table 120 on which the subject 26 is examined and/or a procedure is performed. The coil jigs 152, 154 and 156 can be oriented at various angles relative to the end plates 158, 160. The coil jigs 152, 154 and 156 can be oriented orthogonally to the end plates 158, 160 or at other angles relative to the end plates 158, 160.

Figure 3:
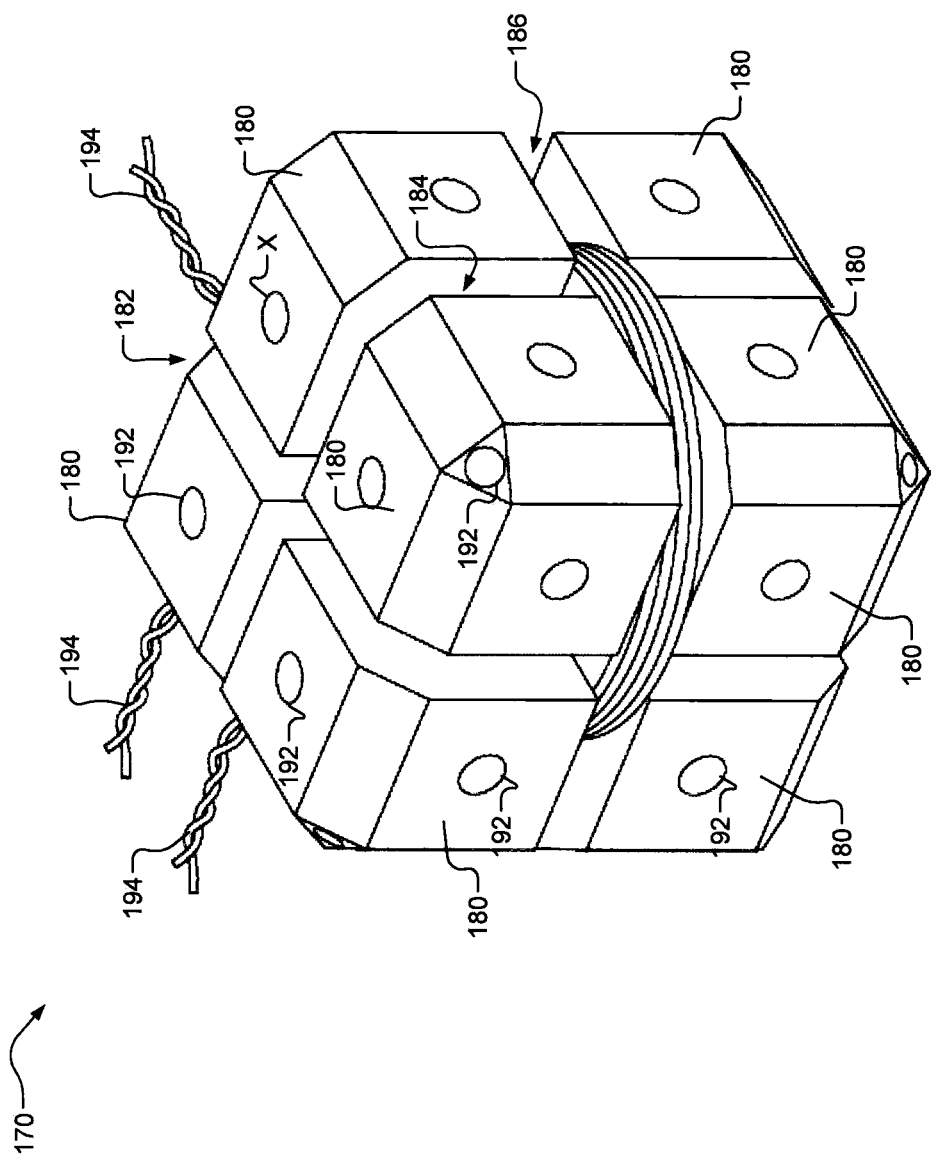
FIG. 3 is a perspective view of a jig with three orthogonally wrapped coils for the transmit coil array of FIG. 2.
Figure 4:
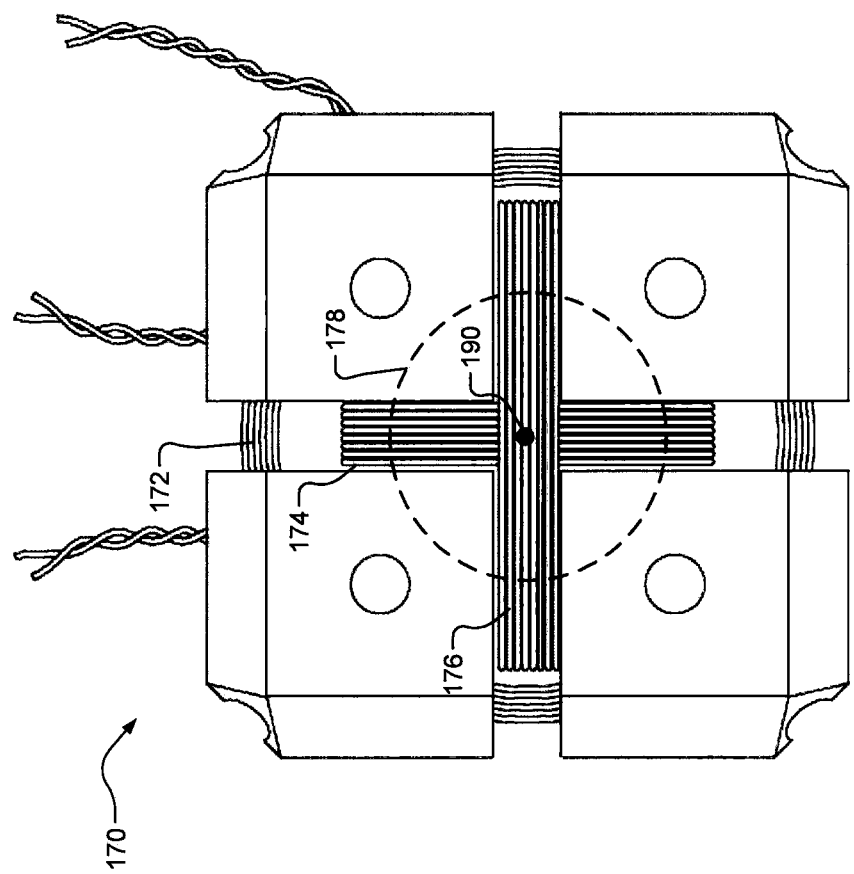
FIG. 4 is a side view of the jig and orthogonally wrapped coils of FIG. 3.

In FIGS. 3-4, a jig 170 and corresponding coils 172, 174, 176 are shown. The jigs 152, 154, 156 of FIG. 2 may be implemented as the jig 170. Although the jig 170 is shown as having three orthogonally positioned coils, any number of coils may be included and may be positioned in various orientations on the jig 170 to provide respective EM fields. An orientation of a coil may refer to a radial wrapping location, an axis of a jig around which the coil is wrapped, coordinates of a center of the coil relative to a center of a corresponding jig, a set of coordinates of the coil relative to a reference point of a TCA or a component (e.g., an end plate or a base plate) of a TCA, an angular position of the coil relative to a component (e.g., an end plate or a base plate) of a TCA, etc.

In the example shown, the jig 170 includes a center member 178 and eight coil-separating blocks 180. The term "block" as used herein may refer to an object having a predetermined shape. Although the coil-separating blocks 180 are shown as having a generally cubular shaped geometry, the coil-separating blocks 180 may have various shaped geometries. The coil-separating blocks 180 protrude away from the center member 178 and form wire wrapping (or coil) channels 182, 184, 186. The coil channels 182, 184, 186 may be externally accessible for wrapping of respective wires to form the coils 172, 174, 176. A single coil channel is provided for each of the coils 172, 174, 176. Each of the coils 172, 174, 176 is wound around the center member 178 and/or a common center point 190 of the jig 170 and in a respective one of the coil channels 182, 184, 186. Each of the coils 172, 174, 176 may have a predetermined number of windings. In one implementation, each of the coils 172, 174, 176 has the same number of windings. In another implementation, the coils 172, 174, 176 have different numbers of windings. Coils on a jig may have the same or a different number of windings than corresponding coils on another jig. The diameter of each of the coil channels 182, 184, 186 of the jig 170 is different and is predetermined such that each of the coils 172, 174, 176 are wrapped on the jig 170 without contacting other ones of the coils 172, 174, 176.

Sides of the jig 170 may include, for example, tabs and/or holes 192, as shown. The tabs and/or holes 192 may be located in the coil-separating blocks 180 and accessible from external surfaces of the coil-separating blocks 180. The coil-separating blocks 180 may each have any number of external surfaces at various angles and/or positions relative to the center member 178 and the center point 190. The tabs and/or holes 192 may be used to attach the jig 170 to corresponding mounting (or end) plates, as shown in FIG. 2. The tabs and/or holes 192 may also be used to hold the jig 170 during wrapping of the wires onto the jig 170. The jig 170 may be held in, for example, a fixture, a gripper, and/or a vice during the wrapping of the wires.

Ends 194 of the wires on the jig 170 may be received into corresponding connectors. Example connectors are shown in FIGS. 6-11. The connectors may be connected to the CAC 54 via the NDI 56 and/or to a processor, controller, and/or control module of an EM navigation system (e.g., the EM navigation system 20).

Figure 5:
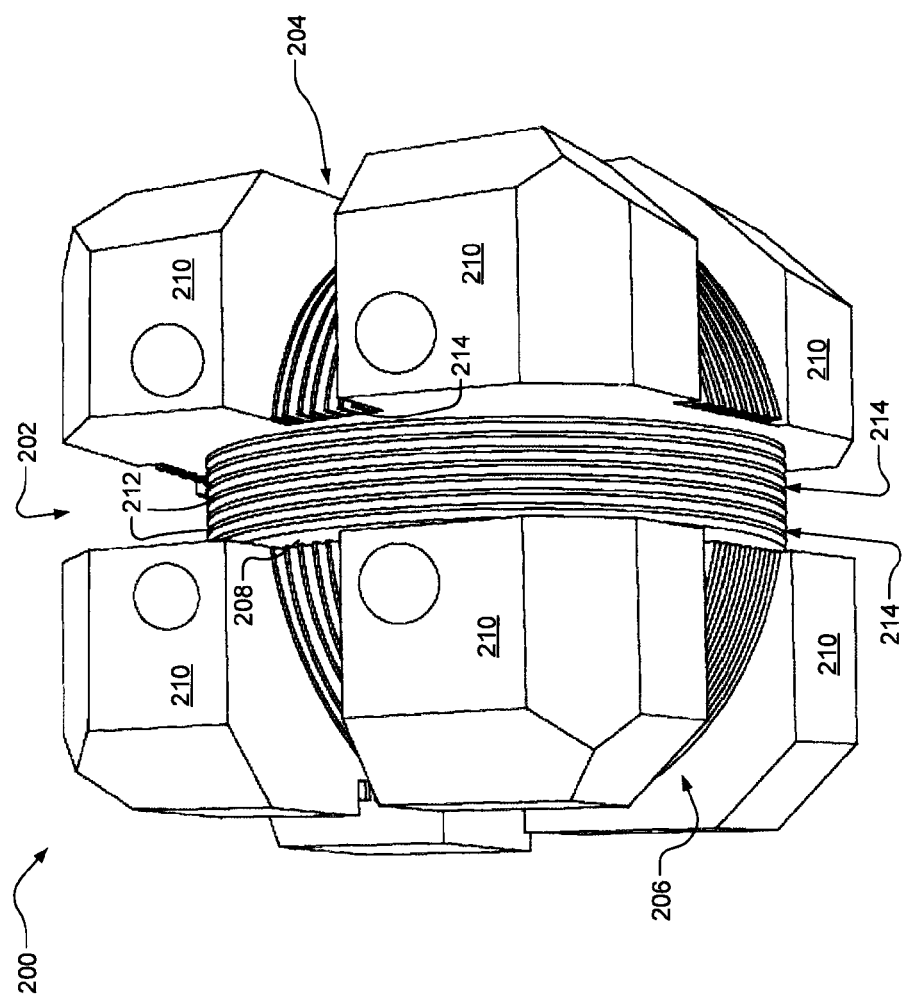
FIG. 5 is a perspective view of a jig having divided wrapping channels in accordance with the present disclosure.

FIG. 5 shows a jig 200 having divided wire wrapping channels (or coil channels) 202, 204, 206. The jig 200 includes a center member 208 and protruding coil-separating blocks 210. Each of the coil channels 202, 204, 206 may have predetermined dimensions including widths and depths. Each of the coil channels 202, 204, 206 is configured to receive a respective coil and is divided by dividers 212 to form multiple wire wrapping channels (or wire channels) 214. The dividers 212 may each have a predetermined width, outer circumference, and/or diameter. The wire channels 214 may each have predetermined widths, depths, inner circumferences, and inner diameters. The dimensions of the coil channels 202, 204, 206, the dividers 212, and the wire channels 214 may be predetermined based on, for example, predetermined levels of current to be applied to the corresponding coils, predetermined operating temperatures of the coils, and/or predetermined EM field characteristics (e.g., electric and/or magnetic vector field values).

Each of the coil channels 202, 204, 206 has a set of dividers (respective ones of the dividers 212) and a set of wire channels (respective ones of the wire channels 214). Each of the sets of dividers may have a respective diameter. Each of the sets of wire channels may have a respective inner diameter and outer diameter, where the outer diameter matches the diameter of the corresponding dividers.

The dividers 212 extend radially outward from the center member 208 and are segregated by the coil channels 202, 204, 206 such that the dividers 212 are non-contiguous annularly and/or toroidally-shaped discs. The dividers 212 and wire channels 214 can provide stacked layers of alternating coil windings and dividers. The elements of the jig 200 including the protruding coil-separating blocks 210, the center member 208 and the dividers 212 may be separate elements or may be implemented as a unitary structure, as shown. Although the jig 200 is shown as being generally cube-shaped, the jig 200 may have a different shape.

Each of the wire channels 214 is configured to receive a wire of a coil. A wire may be wrapped one or more times around the center member 208 and in each of the wire channels 214. In this implementation, the dividers 212 separate each winding of a coil or sets of windings of a coil for precise wrapping of the wire of the coil on the jig 200. Each set may have the same number of windings or may have a respective number of windings. This provides accurate, predictive, consistent placement of each winding of the coil.

The jigs of FIGS. 2-6 allow for iterative manufacturing of a TCA such that multiple TCAs satisfying the same requirements and having the same dimensions can be produced with predictable and consistent characteristics. These characteristics can include jig dimensions, wire lengths, number of windings per coil, number of windings between adjacent dividers of a jig, coil and winding placements, and coil dimensions (width, inner and outer diameters, and thickness).

Figure 6:
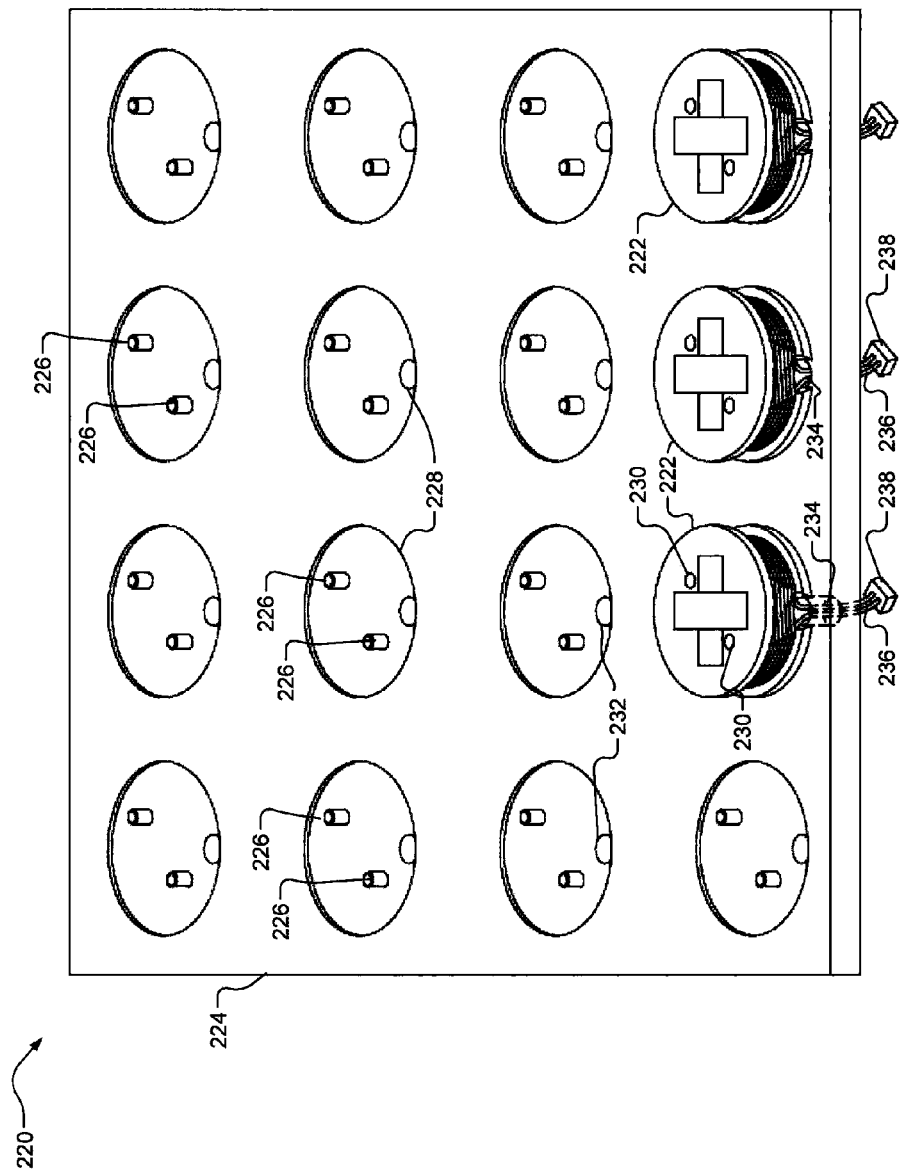
FIG. 6 is a perspective view of a transmit coil array including multiple jigs each having a respective coil in accordance with the present disclosure.

FIG. 6 shows another TCA 220 that includes multiple jigs 222. The TCA 220 may replace the TCA 52 of FIG. 1 and be attached to the table 120 on which the subject 26 is examined and/or a procedure is performed. Each of the jigs 222 is a single-coiled jig with a respective coil. The jigs 222 are mounted in respective locations on a base plate 224. The base plate 224 may have tabs (or holes) 226 and/or recessed sections 228 for accurate placement of jigs on the base plate 224. The tabs (or holes) 226 align with holes (or tabs) 230 in the jigs 222. The recessed sections 228 may have holes 232 through which wires 234 on the jigs may extend, as shown. Ends 236 of the wires 234 on each of the jigs may be received into corresponding connectors 238, which may be on opposite sides of the base plate 224 than the jigs. The connectors 238 may be connected to the CAC 54 via the NDI 56 and/or to a processor, controller, and/or control module of the EM navigation system 20 of FIG. 1. Although in FIG. 6 three jigs and/or twelve recessed sections are shown, the TCA 220 may have any number of jigs and corresponding recessed sections.

Figure 12:
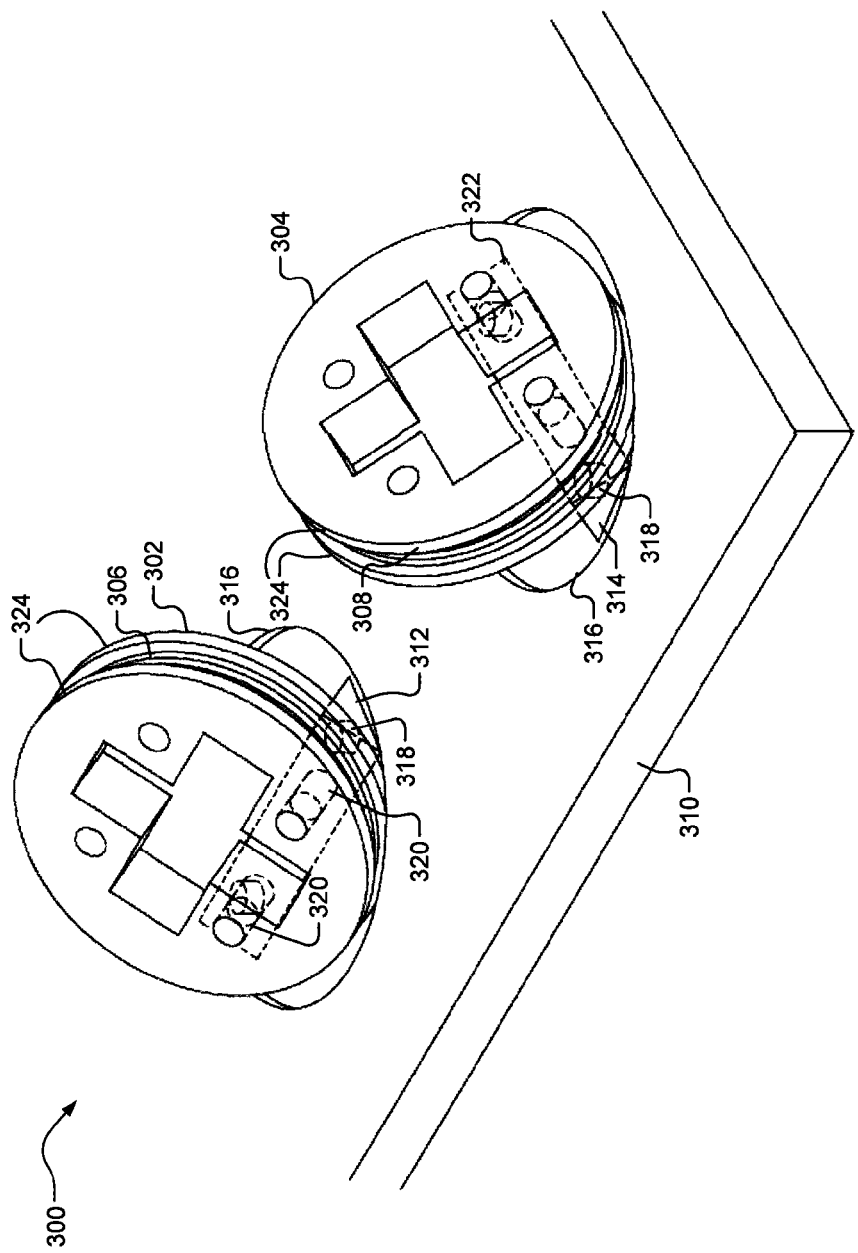
FIG. 12 is a perspective view illustrating a portion of a transmit coil array with single coiled jigs mounted in respective orientations and in accordance with the present disclosure.

Although the three jigs 222 shown have the same orientation on the base plate 224, the jigs of the TCA 220 may have different orientations. An example of jigs having different orientations is shown in FIG. 12. The coils of the jigs that have the same orientation can be used to provide a single EM field. EM field energy generated by the coils having the same orientation add together to increase the size of the EM field. Coils of jigs having different orientations can be used to provide multiple EM fields having different electric and magnetic field vectors extending in respective directions. This allows for increased field diversity.

Figure 7:
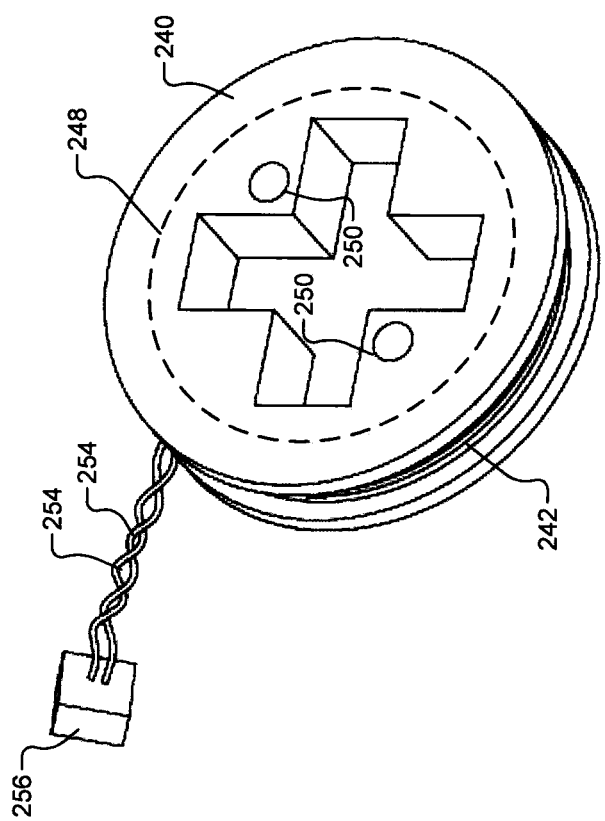
FIG. 7 is a perspective view of a jig and a corresponding coil for the transmit coil array of FIG. 6.
Figure 8:
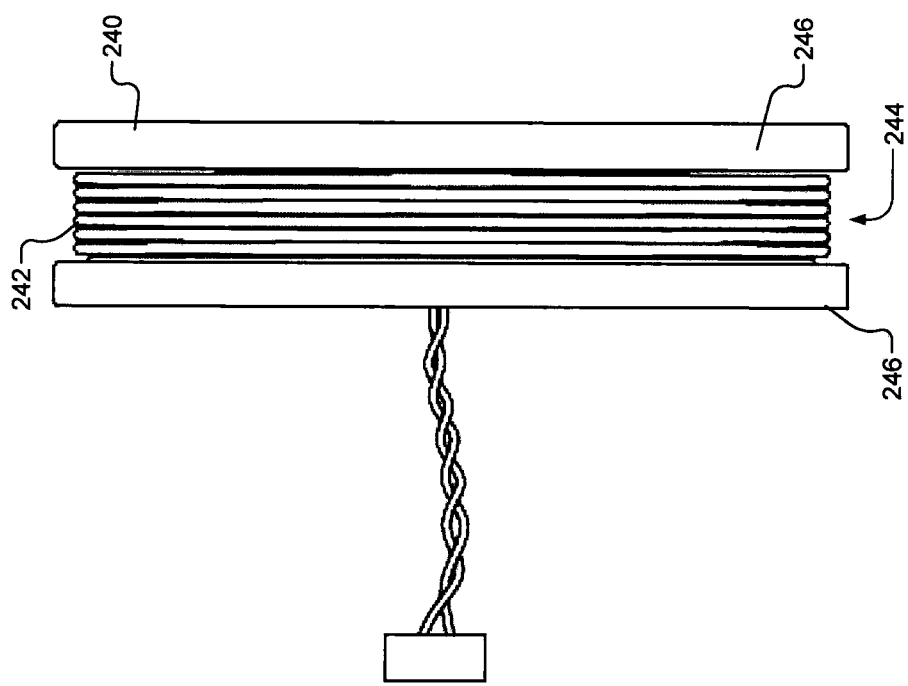
FIG. 8 is a side view of the jig and coil of FIG. 7.

Although the jigs of FIG. 6 are shown as having a single coil with a single coil orientation, each of the jigs may have any number of coils with different orientations. A first example of a jig that may be used in the TCA 220 of FIG. 6 is shown in FIGS. 7-8. A second example of a jig that may be used in the TCA 220 of FIG. 6 is shown in FIGS. 9-11.

FIGS. 7-8 show a jig 240 and a corresponding coil 242. The jig 240 is shown as being cylindrical in shape with a coil channel 244 located between two end members 246. A wire is wrapped around a center member 248 and inner circumference of the coil channel 244. The jig 240 may have holes (or tabs) 250 for mounting on a base plate (e.g., the base plate 224 of FIG. 6) and/or for use in holding the jig 240 during wrapping of a wire on the jig 240 to form the coil 242. The jig 240 may also have a center opening 252 for mounting the jig 240 on a wrapping fixture, bracket, coupling, or rod. As an example, the center opening 252 may be cross-shaped (or irregular prism shaped), as shown, to receive a jig mounting portion of a fixture. The jig mounting portion may be rotated to facilitate in wrapping the wire on the jig 240 to form the coil 242. Ends 254 of the wire may be received by a connector 256.

Figure 9:
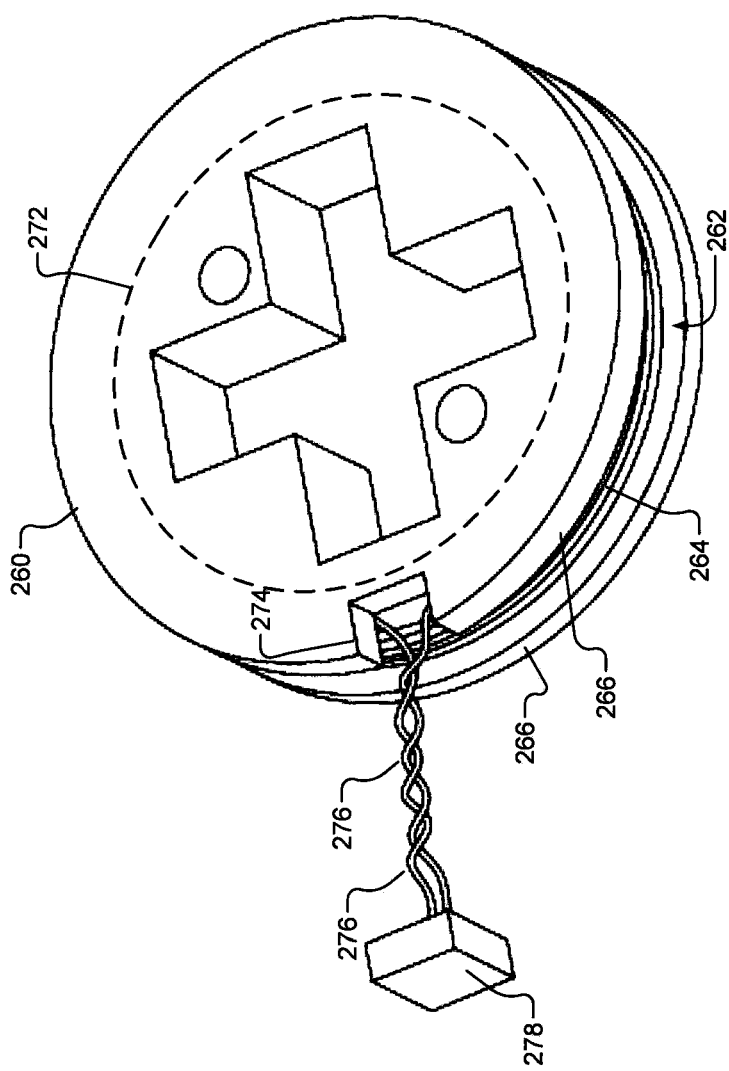
FIG. 9 is a perspective view of a jig with a divided coil channel and a corresponding coil in accordance with the present disclosure.
Figure 10:
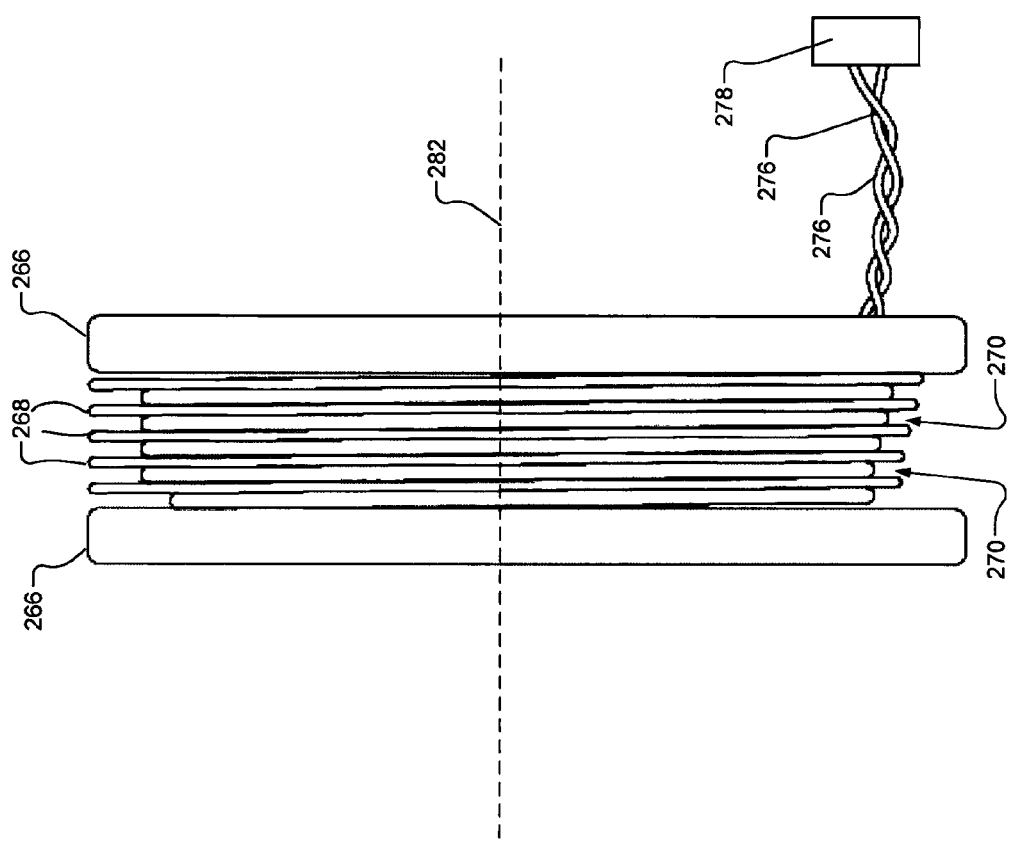
FIG. 10 is a side view of the jig and coil of FIG. 9.
Figure 11:
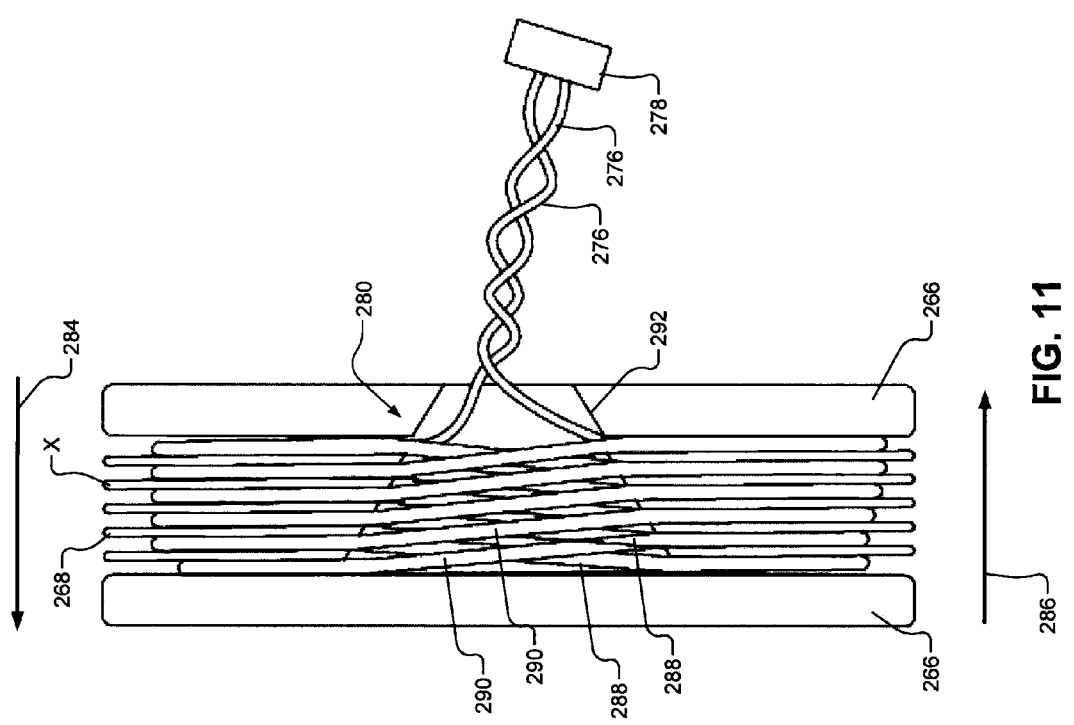
FIG. 11 is a side view of the jig and coil of FIG. 9 illustrating a crossover section in accordance with the present disclosure.

FIGS. 9-11 show a jig 260 with a coil channel 262 and a corresponding coil 264. The coil channel 262 is between end members 266. The coil channel 262 includes dividers 268 and wire channels 270. The dividers 268 extend radially outward from a center member 272. The end members 266, the center member 272 and the dividers 268 may be separate elements or may be implemented as a unitary structure, as shown. One of the end members 266 may include a hole or a notch 274, as shown in FIG. 9. Ends 276 of a wire wrapped on the jig 260 may extend through the notch 274 and be received by a connector 278. This allows for the wire to be passed through a hole in, for example, a base plate.

The jig 260 may have a crossover section 280 between the end members 266 and separating each of the dividers 268, such that the dividers 268 are non-contiguous annularly and/or toroidally-shaped discs. The wire, when wrapped on the jig 260, may be wrapped around the center member 272, around a center axis 282, in the wire channels 270 and in a first direction parallel (indicated by arrow 284) to the center axis 282. The wire may then be wrapped in a second direction (indicated by arrow 286) opposite the first direction. To facilitate wrapping in the first direction and second direction the wire may switch between wire channels in the crossover section 280. First portions 288 of the wire extend through the crossover section 280 while wrapping the wire in the first direction. Second portions 290 of the wire extend through the crossover section 280 while wrapping the wire in the second direction. The second portions 290 may crossover the first portions 288 in the crossover section 280. Portions of the EM field generated by the portions 288, 290 of the coil in the crossover section 280 may cancel each other.

The crossover section 280 may be wedge-shaped with a narrow end 292 extending through one of the end members 266. This allows ends 276 of the wire to (i) extend through the end member and, for example, a base plate, and (ii) be received by the connector 278. The crossover section 280 allows for accurate positioning of crossover locations. Crossover locations refer to locations in the crossover section 280 in which the wire transitions between two of the wire channels 270.

Although not shown, one or more of the wires of the coils on the jigs of FIGS. 3-5 may be wrapped in multiple directions and perform crossovers similar to the wire of FIG. 11. For example a first wire may crossover between wire channels in spaces (or gaps) provided by a second coil channel.

FIG. 12 shows a portion 300 of a TCA with single coiled jigs 302, 304 mounted in respective orientations. The jigs 302, 304 and corresponding coils 306, 308 are shown mounted on a base plate 310 in different orientations. The jigs 302, 304 are angled upward from the base plate 310 via orienting blocks 312, 314. For example only, the orienting blocks 312, 314 may be triangular prism shaped and mounted on the base plate 310. The orienting blocks 312, 314 may be located in recessed sections 316 of the base plate 310 and may have first holes (or tabs) 318, which are attached to second tabs (or holes) on the base plate 310. The orienting blocks 312, 314 may have third tabs (or holes) 320, which connect to fourth holes (or tabs) on the jigs 302, 304. The orienting blocks 312, 314 may be adhered via an adhesive to the base plate 310 and/or the jigs 302, 304. Although plates, jigs and orienting blocks are described herein as being connected via tabs and corresponding holes, the plates, jigs, and orienting blocks may be connected to each other via other suitable techniques.

The orienting blocks 312, 314 have jig mounting surfaces 322. Directional placement of the orienting blocks 312, 314 and angles of the jig mounting surfaces 322 relative to the base plate 310 may be predetermined to set the orientation of the jigs 302, 304 and corresponding coils 306, 308. End members 324 of the jigs 302, 304 may be at the same angles relative to the base plate 310 as the corresponding jig mounting surfaces 322. This allows coils to not be wrapped around the same center member of the same jig and be placed in various positions and/or orientations relative to each other. As an example, the coils 306, 308 may be orthogonally positioned relative to each other and/or be used to generate orthogonal EM fields. Any number of jigs and coils may be included in the TCA. The jigs 302, 304 and coils 306, 308 may have the same or different orientations. In one implementation, more than two jigs and coils have the same orientation and more than two jigs and coils have different orientations.

In one implementation, twelve jigs and corresponding coils are included. The twelve jigs and twelve coils include three sets. Each of the sets includes four jigs and four coils. The jigs and coils of a single set are orientated in the same direction (e.g., have center axes that are in parallel with each other). A center axis being an axis around which a coil is wrapped. The jigs and coils of different sets are oriented differently (e.g., have center axes that are not in parallel with each other).

Each of the jigs and corresponding coils of FIGS. 2-12 may be referred to collectively as an EM device. Although the jigs and/or EM devices of FIGS. 2-12 are shown as having a single coil and wire for each coil channel, the jigs and/or EM devices may have more than one coil and/or wire in each coil channel. Also, although the coils and corresponding coil channels and center members of FIGS. 2-12 are circular shaped, the coils and corresponding coil channels and center members may be shaped differently. For example, the coils and corresponding coil channels and center members may be square shaped, rectangular shaped, elliptical shaped, and/or polygonally shaped.

The jigs, end plates, and base plates of FIGS. 2-12 and/or other jigs, end plates, and/or base plated disclosed herein may be formed of, for example, thermally stable plastic and/or ceramic. This allows these components to: withstand expansions and/or contractions of coils due to temperature changes of the coils; maintain structural integrity during changes in temperatures of the coils and the components; and to maintain respective dimensions within predetermined ranges during changes in the temperatures. The jigs, end plates, and base plates disclosed herein may be formed of, for example, nylon, polyvinylchloride, polycarbonate, polyester, polysulphone, polyphenylenesulphone, polyetheretherketone, polyphenylene, sulphide, polyetherimide, polyamide-imide, and/or polybenzimidazole. The materials of the jigs, end plates, and base plates may have coefficients of thermal expansion that are less than predetermined values. The jigs, end plates, and base plates disclosed herein may be constructed using injection molding, machining, and/or rapid prototyping. As an example, the jigs, end plates, and base plates disclosed herein may be formed using, for example, stereolithography. As another example, alumina ceramic may be printed using a stereolithography process or a cast process to form one or more of the jigs, end plates, and base plates disclosed herein.

Figure 13:
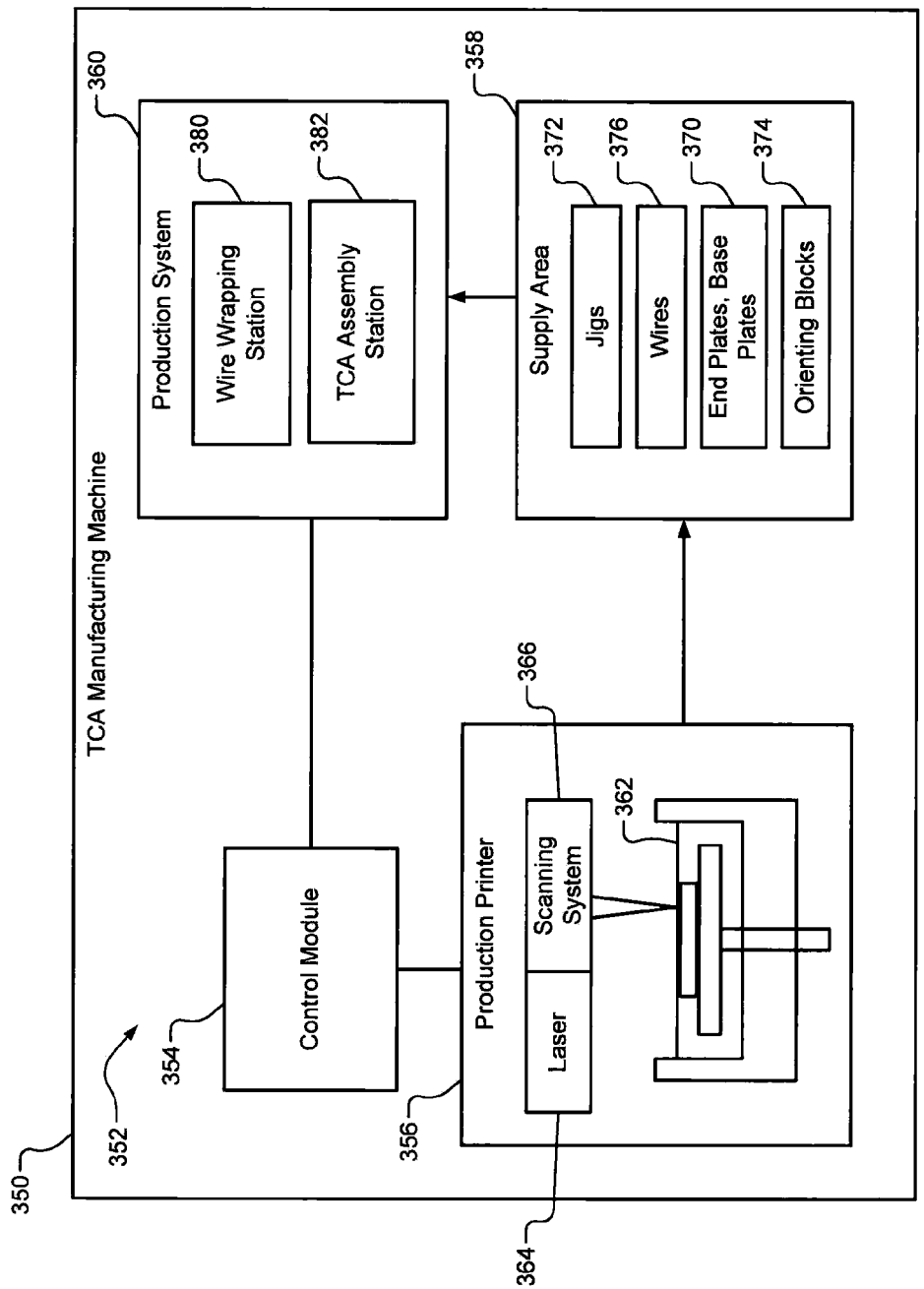
FIG. 13 is a transmit coil array manufacturing machine in accordance with an embodiment of the present disclosure.

FIG. 13 shows a TCA manufacturing machine 350 that includes a manufacturing system 352. The TCA manufacturing machine 350 and manufacturing system 352 are provided as an example, the plates, jigs, TCAs, and orienting blocks disclosed herein may be formed and/or assembled using other suitable techniques. The TCA manufacturing machine 350 and the manufacturing system 352 may include a control module 354, a production printer 356, a supply area 358, and a production system 360. Each of the control module 354, the production printer 356, the supply area 358, and the production system 360 may be included in the TCA manufacturing machine 350 and/or the manufacturing system 352 or may be separate from the TCA manufacturing machine 350 and the manufacturing system 352.

The control module 354 may control operations in the production printer 356, supply area 358 and/or production system 360 and/or may be in communication with modules in the production printer 356, supply area 358 and/or production system 360. The production printer 356, supply area 358 and/or production system 360 may have respective control modules or may share a single control module, as shown.

The production printer 356 may be, for example, a stereolithography printer or other type of production printer or production machine. The production printer 356 may include, for example, a resin bath 362 in which plates, jigs and/or orienting blocks may be formed via a laser 364 and scanner system 366. The plates, jigs and/or orienting blocks may be stored in the supply area 358.

The supply area may store plates 370, jigs 372, orienting blocks 374 and wires 376 and include motors, grippers, and/or other machinery to move the plates 370, jigs 372, orienting blocks 374 and/or wires 376 from the production printer 356 to the supply area 358 or from the supply area 358 to the production system 360. The wires 376 may be pre-cut to predetermined lengths or may be cut as used in the production system 360.

The production system 360 may include a wire wrapping station 380 and a TCA assembly station 382 and corresponding grippers and/or motors to move, wire wrap and connect the jigs 372 to the plates 370. The jigs 372 may be wrapped in the wire wrapping station 380 and mounted between end plates, on a base plate and/or in housing in the TCA assembly station 382. The production system 360 may include wire cutters for cutting wires to predetermined lengths.

Figure 14:
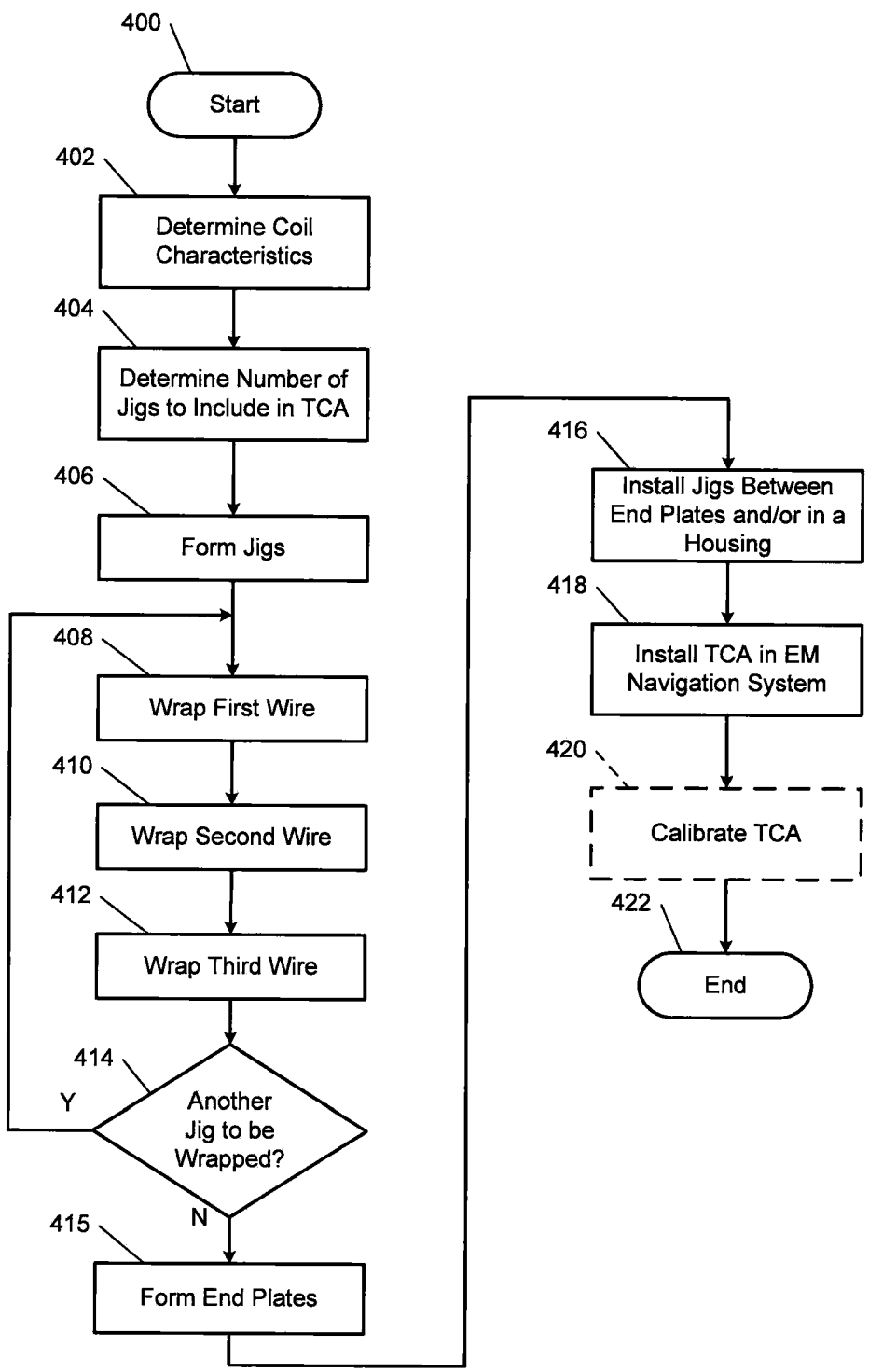
FIG. 14 illustrates a method of manufacturing and installing the transmit coil array of FIG. 2 in accordance with the present disclosure.

FIG. 14 shows a method of manufacturing and installing the TCA of FIG. 2. Although the following tasks are primarily described with respect to the implementations of FIGS. 2-5, the tasks may be easily modified to apply to other implementations of the present disclosure. The tasks may be iteratively performed as part of an automated process. Any of the tasks may be performed manually and/or by a TCA manufacturing machine (e.g., the TCA manufacturing machine 350 of FIG. 13) and/or assembly line controlled by one or more control modules (referred to below as "the control module"). The method may begin at 400.

At 402, coil characteristics are determined. The coil characteristics may include, for example, lengths of wires, number of windings per coil, number of windings per wire channel, etc.

At 404, a number of jigs to be included in a TCA and corresponding dimensions of the jigs are determined. This may be based on the coil characteristics, a number of jigs per EM field to be generated, a number of EM fields to be generated, a maximum current level or current ranges of corresponding coils, and characteristics of EM fields to be generated.

At 406, the jigs (e.g., the jigs of FIGS. 2-5) are formed having the predetermined dimensions to provide mounting locations for coils having predetermined shapes and orientations relative to each other and the jigs.

At 408, a first wire is wrapped on one of the jigs (referred to in the below tasks 410, 412 as "the jig"), in a first coil channel, and around a center member and a center point of the jig to form a first coil. The first wire is wrapped according to corresponding and predetermined coil characteristics.

At 410, a second wire is wrapped on the jig, in a second coil channel, and around (i) the center member, (ii) the center point, and (iii) the first coil. The second wire may be wrapped, such that the second coil is at a predetermined position relative to the first coil. The second wire is wrapped according to corresponding and predetermined coil characteristics.

At 412, a third wire is wrapped on the jig, in a third coil channel, and around (i) the center member, (ii) the center point, (iii) the first coil, and (iv) the second coil. The third wire may be wrapped, such that the third coil is at a predetermined position relative to the first coil and the second coil. The third wire is wrapped according to corresponding and predetermined coil characteristics.

Although the above tasks include three wire wrapping tasks, any number of wire wrapping tasks may be included.

At 414, the control module determines whether there is another jig to be wrapped. If there is another jig to be wrapped, task 408 is performed, otherwise task 416 is performed.

At 415, the end plates are formed. At 416, the one or more jigs may be installed between end plates (e.g., the end plates) and/or mounted within a housing to form the TCA. The jigs may be press-fitted, adhesively attached and/or connected to the end plates.

At 418, the TCA may be installed in an EM navigation system (e.g., the EM navigation system 20). At 420, the TCA may be calibrated via the navigation computer 40 or other controller, processor and/or control module of the EM navigation system. In one implementation, task 420 is not performed. The TCA is then used in a procedure with having been calibrated. The EM navigation system may perform the procedure based on predetermined characteristics of the TCA, components of the TCA (coils, jigs, plates, etc.), and EM field characteristics (e.g., electric and magnetic field vector values). The characteristics of the TCA may include any of the TCA characteristics disclosed herein including dimensions and characteristics of the components in the TCA. The method may end at 422.

Figure 15:
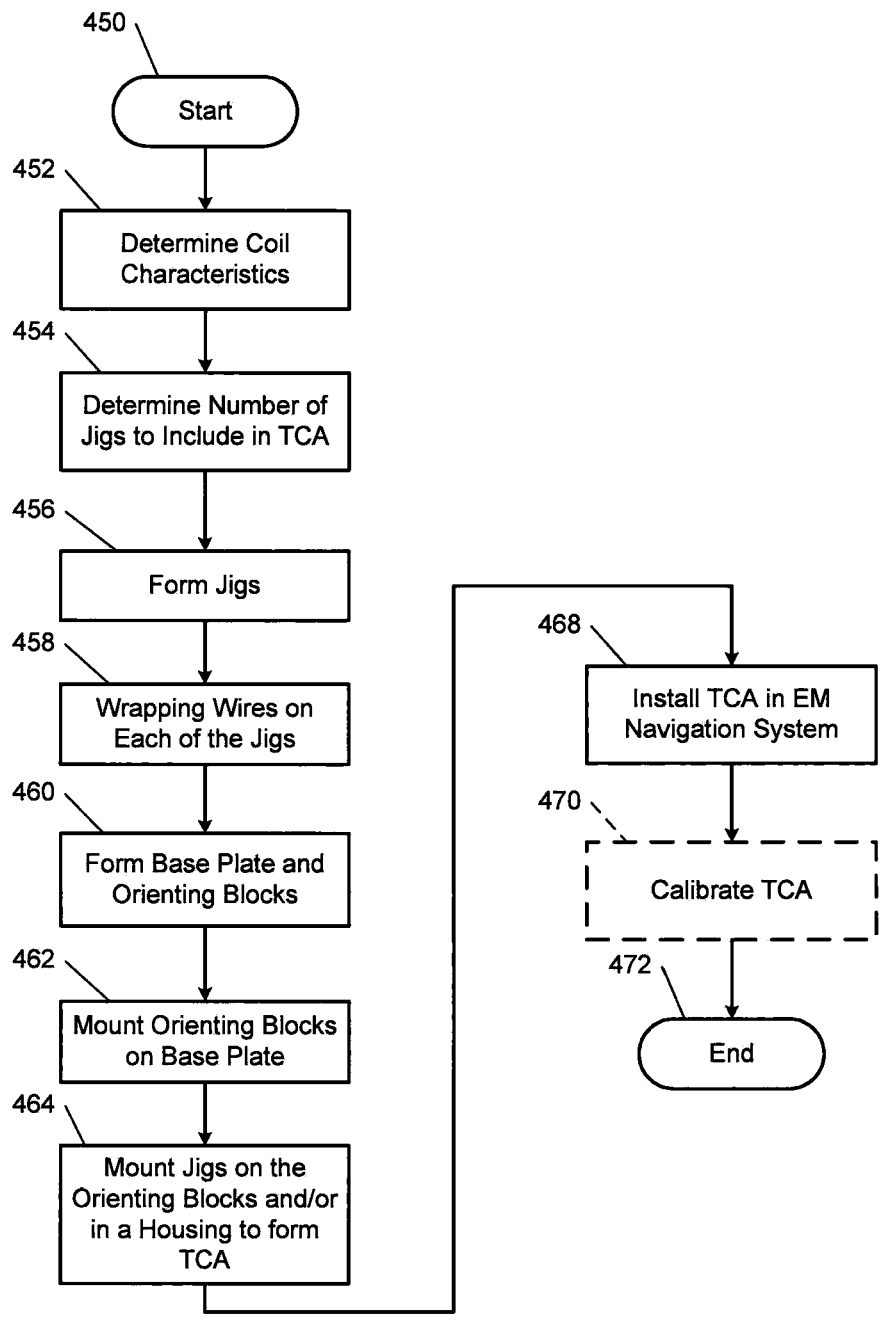
FIG. 15 illustrates a method of manufacturing and installing the transmit coil arrays of FIGS. 6 and 12 in accordance with the present disclosure.

FIG. 15 shows a method of manufacturing and installing the TCAs of FIGS. 6 and 12. Although the following tasks are primarily described with respect to the implementations of FIGS. 6-12, the tasks may be easily modified to apply to other implementations of the present disclosure. The tasks may be iteratively performed as part of an automated process. The tasks may be performed by a TCA manufacturing machine (e.g., the TCA manufacturing machine 350 of FIG. 13) and/or assembly line controlled by one or more control modules. The method may begin at 450.

At 452, coil characteristics are determined. The coil characteristics may include, for example, lengths of wires, number of windings per coil, number of windings per wire channel, etc.

At 454, a number of jigs to be included in a TCA and corresponding dimensions of the jigs are determined. This may be based on the coil characteristics, a number of jigs per EM field to be generated, a number of EM fields to be generated, a maximum current level or current ranges of corresponding coils, and characteristics of EM fields to be generated.

At 456, the jigs (e.g., the jigs of FIGS. 2-5) are formed having the predetermined dimensions to provide mounting locations for coils having predetermined shapes and orientations relative to each other and the jigs.

At 458, wrapping respective wires on each of the jigs formed at 454. The wires may be wrapped in respective coil channels and/or wire channels of the jigs. Each of the wires is wrapped according to corresponding and predetermined coil characteristics.

At 460, a base plate and/or orienting blocks are formed. The orienting blocks may be formed at 460 as part of the base plate or may be formed at 454 as part of the jigs. The orienting blocks are formed with jig mounting surfaces at predetermined angles.

At 462, the orienting blocks may be mounted on the base plate at predetermined positions. At 464, the jigs may be mounted on the orienting blocks and/or mounted within a housing to form the TCA. The jigs are mounted on the orienting blocks in predetermined positions and to place the jigs and wires in predetermined orientations relative to the base plate.

At 466, the TCA may be installed in an EM navigation system (e.g., the EM navigation system 20). At 468, the TCA may be calibrated via the navigation computer 40 or other controller, processor and/or control module of the EM navigation system. In one implementation task 468 is not performed. The EM navigation system may perform the procedure based on predetermined characteristics of the TCA, components of the TCA (coils, jigs, plates, orienting blocks, etc.), and EM field characteristics (e.g., electric and magnetic field vector values). The characteristics of the TCA may include any of the TCA characteristics disclosed herein including dimensions and characteristics of the components in the TCA. The method may end at 470.

The above-described tasks of FIGS. 14 and 15 are meant to be illustrative examples; the tasks may be performed sequentially, synchronously, simultaneously, continuously, during overlapping time periods or in a different order depending upon the application. Also, any of the tasks may not be performed or skipped depending on the implementation and/or sequence of events.

The above-described implementations, allow for coils to be wound on jigs in a consistent and repeatable manner. This allows for a reduction in calibration time of TCAs and/or elimination of a calibration process due to the predictable physical and operating characteristics of the TCAs.

The wireless communications described in the present disclosure can be conducted in full or partial compliance with IEEE standard 802.11-2012, IEEE standard 802.16-2009, IEEE standard 802.20-2008, and/or Bluetooth Core Specification v4.0. In various implementations, Bluetooth Core Specification v4.0 may be modified by one or more of Bluetooth Core Specification Addendums 2, 3, or 4. In various implementations, IEEE 802.11-2012 may be supplemented by draft IEEE standard 802.11ac, draft IEEE standard 802.11ad, and/or draft IEEE standard 802.11ah.

It should be understood that one or more steps within a method may be executed in different order (or concurrently) without altering the principles of the present disclosure.

In this application, including the definitions below, the term module may be replaced with the term circuit. The term module may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip.

The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this application may be partially or fully implemented by one or more computer programs executed by one or more processors. The computer programs include processor-executable instructions that are stored on at least one non-transitory tangible computer readable medium. The computer programs may also include and/or rely on stored data.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise.

Terms such as "first," "second," and other numerical terms when used herein do not imply a sequence or order unless clearly indicated by the context. Thus, a first element, component, region, layer or section discussed herein could be termed a second element, component, region, layer or section without departing from the teachings of the example embodiments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A transmit coil array comprising:
a plurality of electromagnetic devices, each electromagnetic device comprising,
a jig having
a pair of end members, and
a center member disposed between the pair of end members, wherein the pair of end members and the center member together provide a coil channel, wherein the coil channel comprises dividers, and wherein the center member, the dividers, and the end member together provide wire channels; and
a wire wrapped on the center member and in the wire channels to provide a coil, wherein the coil is configured to connect to an electromagnetic navigation system and generate an electromagnetic field to be emitted relative to a subject,
wherein the wire is wrapped in the wire channels in opposing first and second directions to provide a plurality of respective winding layers;
wherein the jig comprises a crossover section in which the wire is switched between two of the wire channels, the crossover section separates each divider, such that each divider is non-contiguous annularly where the wire crosses itself a plurality of times in the crossover section upon increasing the winding layer; and
a base plate, wherein the plurality of electromagnetic devices are mounted on the base plate and in respective orientations.

2. The transmit coil array of claim 1, wherein each jig includes at least one of a plastic material and a ceramic material.

3. The transmit coil array of claim 1, further comprising orienting blocks mounted on the base plate and between the jigs of the electromagnetic devices and the base plate, wherein:
orienting blocks comprise jig mounting surfaces on which the jigs of the electromagnetic devices are mounted; and
the jigs and the wires are oriented relative to each other and relative to the base plate based on angles of jig mounting surfaces relative to the base plate.

4. The transmit coil array of claim 3, wherein:
the base plate comprise first tabs;
the first tabs are inserted into respective holes in the orienting blocks;
the orienting blocks comprise second tabs; and
the second tabs are inserted into respective holes in the jigs.

5. The transmit coil array of claim 1, wherein:
the jigs comprise notches;
the base plate comprises holes; and
the wires extend through the notches of the jigs and the holes in the base plate.

6. A system comprising:
the transmit coil array of claim 1;
a controller configured to generate first signals via coils of the transmit coil array without previous calibration of the transmit coil array; and
a tracking device configured to (i) receive the first signals, and (ii) generate second signals based on the first signals,
wherein the controller is configured to track a position of the tracking device based on the second signals and during a procedure on the subject.

7. The transmit coil array of claim 1, wherein the crossover section is wedge-shaped with a narrow end extending through one of the end members to allow the wire to extend through the one of the end members.

8. A transmit coil array comprising:
a first jig having a first pair of end members and a first center member disposed between the first pair of end members, wherein the first pair of end members and the first center member together provide a first coil channel;
a first wire wrapped on the first center member and within the first coil channel to provide a first coil, wherein the first coil is configured to connect to an electromagnetic navigation system and generate an electromagnetic field to be emitted relative to a subject;
a second jig having a second pair of end members and a second center member disposed between the second pair of end members, wherein the second pair of end members and the second center member together provide a second coil channel;
a second wire wrapped on the second center member and within the second coil channel to provide a second coil, wherein the second coil is configured to connect to an electromagnetic navigation system and generate an electromagnetic field to be emitted relative to a subject; and
a base plate, wherein the first jig having the first coil is mounted on the base plate in a first orientation and the second jig having the second coil is mounted on the base plate in a second orientation, the first orientation different from the second orientation;
wherein the first coil channel includes first dividers such that the first center member, the first dividers, and the first pair of end members together provide a first plurality of wire channels and wherein the first wire is wrapped in the first plurality of wire channels to provide the first coil,
wherein the first wire is wrapped in the first plurality of wire channels in opposing first and second directions to provide a plurality of respective first winding layers;
wherein the first jig includes a first crossover section in which the first wire is switched between two of the first plurality of wire channels, the first crossover section separating each of the first dividers, such that each of the first dividers is non-contiguous annularly where the first wire is switched between two of the first plurality of wire channels upon increasing the first winding layer.

9. The transmit coil array of claim 8, wherein the first wire crosses itself a plurality of times in the first crossover section.

10. The transmit coil array of claim 8, further comprising a first orienting block mounted on the base plate and between the first jig and the base plate and a second orienting block mounted on the base plate and between the second jig and the base plate, wherein the first orienting block orients the first jig in the first orientation and the second orienting block orients the second jig in the second orientation.

11. The transmit coil array of claim 10, wherein the first orienting block includes first jig mounting surfaces in which the first jig is mounted, where the first jig mounting surfaces are at an angle relative to the base plate, wherein the first jig and the first coil is oriented in the first orientation relative to the base plate based on the angle of the first jig mounting surfaces.

12. The transmit coil array of claim 11, wherein:
the base plate comprise first tabs;

the first tabs are inserted into respective holes in the first orienting block;

the first orienting block comprises second tabs; and the second tabs are inserted into respective holes in the first jig.

13. The transmit coil array of claim 8, wherein the first jig and the base plate include tabs and recesses for securing the first jig to the base plate.

14. The transmit coil array of claim 8, wherein the first jig defines a cruciform shaped center opening configured for mounting the first jig on a wrapping fixture.

15. The transmit coil array of claim 8, wherein the first jig and the second jig and the first coil and the second coil include twelve jigs and twelve coils with three sets, each set includes four jigs and four coils wherein the four jigs and four coils in each set are oriented in the same direction.

16. The transmit coil array of claim 8, wherein the first jig includes at least one of a plastic material and a ceramic material.

17. The transmit coil array of claim 8, wherein the crossover section is wedge-shaped with a narrow end extending toward one of the first pair of end members.

18. The transmit coil array of claim 17, wherein the narrow end extends through the one of the first pair of end members to allow the first wire to extend through the one of the first pair of end members.

19. A transmit coil array comprising:
a jig having
 a pair of end members,
 a center member disposed between the pair of end members,
 a plurality of dividers radially extending from the center member to define a plurality of wire channels,
 a crossover section formed on the center member to define an area on the center member separating each of the plurality of dividers such that each of the plurality of dividers is non-contiguous annularly;
a wire wrapped on the center member to form a coil, where the wire is switched between two of the plurality of wire channels in the crossover section, wherein the wire is wrapped in the plurality of wire channels in opposing first and second directions to provide a plurality of respective winding layers;
wherein the coil is configured to operate with an electromagnetic navigation system and to generate an electromagnetic field to be emitted relative to a subject; and
a base plate, wherein the jig having the coil is mounted on the base plate.

20. The transmit coil array of claim 19, wherein the crossover section is wedge-shaped with a narrow end extending through one of the end members.

* * * * *